(12) United States Patent
Seyffer et al.

(10) Patent No.: US 8,859,106 B2
(45) Date of Patent: Oct. 14, 2014

(54) USE OF POLYPEPTIDES IN THE FORM OF ADHESIVE AGENTS

(75) Inventors: Hermann Seyffer, Heidelberg (DE); Karl-Heinz Schumacher, Neustadt (DE); Hans-Georg Lemaire, Limburgerhof (DE); Ulf Baus, Dossenheim (DE); Thomas Subkowski, Ladenburg (DE); Marvin Karos, Schwetzingen (DE); Claus Bollschweiler, Heidelberg (DE); Thomas Heidenfelder, Dannstadt-Schauernheim (DE)

(73) Assignee: BASF SE, Ludwigshafen (DE)

( * ) Notice: Subject to any disclaimer, the term of this patent is extended or adjusted under 35 U.S.C. 154(b) by 1639 days.

(21) Appl. No.: 11/886,987

(22) PCT Filed: Mar. 28, 2006

(86) PCT No.: PCT/EP2006/061085
§ 371 (c)(1),
(2), (4) Date: Sep. 24, 2007

(87) PCT Pub. No.: WO2006/103225
PCT Pub. Date: Oct. 5, 2006

(65) Prior Publication Data
US 2009/0233110 A1    Sep. 17, 2009

(30) Foreign Application Priority Data

Mar. 31, 2005 (DE) .................. 10 2005 015 043
Sep. 23, 2005 (DE) .................. 10 2005 045 770

(51) Int. Cl.
| | |
|---|---|
| B32B 9/02 | (2006.01) |
| B05D 3/10 | (2006.01) |
| A61L 27/34 | (2006.01) |
| B32B 15/18 | (2006.01) |
| B32B 15/08 | (2006.01) |
| B32B 25/04 | (2006.01) |
| B32B 15/06 | (2006.01) |
| B32B 7/12 | (2006.01) |
| B32B 25/08 | (2006.01) |
| C08J 7/04 | (2006.01) |
| A61L 31/10 | (2006.01) |
| A61L 24/04 | (2006.01) |
| B32B 27/08 | (2006.01) |
| B32B 15/20 | (2006.01) |

(52) U.S. Cl.
CPC .............. C08J 7/047 (2013.01); *B32B 2307/54* (2013.01); *B32B 2255/26* (2013.01); A61L 27/34 (2013.01); B32B 15/18 (2013.01); B32B 9/02 (2013.01); *B32B 2307/5825* (2013.01); B32B 15/08 (2013.01); B32B 25/042 (2013.01); B32B 15/06 (2013.01); B32B 7/12 (2013.01); B32B 25/08 (2013.01); A61L 31/10 (2013.01); A61L 24/043 (2013.01); B32B 27/08 (2013.01); C08J 2489/00 (2013.01); B32B 15/20 (2013.01)

USPC .......... 428/459; 428/457; 428/458; 427/327; 156/336

(58) Field of Classification Search
None
See application file for complete search history.

(56) References Cited

U.S. PATENT DOCUMENTS

| | | |
|---|---|---|
| 2,399,161 A | 4/1946 | Brother et al. |
| 3,751,280 A | 8/1973 | Nerurkar et al. |
| 4,098,740 A * | 7/1978 | Wallace ................. 524/517 |
| 4,129,706 A | 12/1978 | Keppler et al. |
| 4,241,191 A | 12/1980 | Keppler et al. |
| 5,015,677 A | 5/1991 | Benedict et al. |
| 5,049,504 A | 9/1991 | Maugh et al. |
| 5,110,835 A | 5/1992 | Walter et al. |
| 5,290,819 A | 3/1994 | Witt et al. |
| 5,859,198 A | 1/1999 | Haber |
| 6,977,239 B1 | 12/2005 | Weuthen et al. |
| 2003/0049726 A1 | 3/2003 | Holloway et al. |
| 2003/0113454 A1 | 6/2003 | de Vocht et al. |
| 2003/0134042 A1 | 7/2003 | de Vocht et al. |
| 2003/0217419 A1 | 11/2003 | Vic |
| 2004/0224137 A1* | 11/2004 | Rogalska et al. ............. 428/209 |
| 2005/0058689 A1* | 3/2005 | McDaniel .................... 424/426 |
| 2006/0040349 A1 | 2/2006 | Sweigard et al. |
| 2007/0077619 A1 | 4/2007 | Ostermann et al. |
| 2008/0319168 A1 | 12/2008 | Subkowski et al. |
| 2009/0041922 A1 | 2/2009 | Kühnle et al. |
| 2009/0101167 A1 | 4/2009 | Boeckh et al. |
| 2009/0104663 A1 | 4/2009 | Subkowski et al. |
| 2009/0117796 A1 | 5/2009 | Montag et al. |

(Continued)

FOREIGN PATENT DOCUMENTS

| | | |
|---|---|---|
| DE | 2609104 A1 | 9/1977 |
| DE | 2638839 A1 | 3/1978 |

(Continued)

OTHER PUBLICATIONS

Serimaa et al, Langmuir-Blodgett films of hydrophobins HFBI and HFBII, Surface Science 584 (2005) 35-40.*

(Continued)

*Primary Examiner* — Monique Jackson
(74) *Attorney, Agent, or Firm* — Drinker Biddle & Reath LLP

(57) ABSTRACT

A multilayered composite or coated substrate, comprising compounds of which at least 40% by weight are composed of alpha-amino acids linked via peptide bonds as adhesion promoters between at least two adjacent layers of the composite or between the coating and the substrate.

14 Claims, 3 Drawing Sheets

(56) References Cited

U.S. PATENT DOCUMENTS

| | | | |
|---|---|---|---|
| 2009/0131281 A1 | 5/2009 | Guzmann et al. | |
| 2009/0136433 A1 | 5/2009 | Subkowski et al. | |
| 2009/0136996 A1 | 5/2009 | Subkowski et al. | |
| 2009/0162659 A1 | 6/2009 | Exner et al. | |
| 2009/0232867 A1* | 9/2009 | Domb et al. ............ | 424/423 |
| 2009/0233348 A1 | 9/2009 | Danner et al. | |
| 2009/0241413 A1 | 10/2009 | Subkowski et al. | |
| 2009/0282729 A1 | 11/2009 | Guzmann et al. | |
| 2009/0297884 A1 | 12/2009 | Becker et al. | |
| 2009/0305930 A1 | 12/2009 | Becker et al. | |
| 2010/0044308 A1 | 2/2010 | Baus et al. | |
| 2010/0166627 A1 | 7/2010 | Baus et al. | |
| 2010/0170142 A1 | 7/2010 | Posselt et al. | |
| 2010/0240774 A1 | 9/2010 | Subkowski et al. | |
| 2010/0317833 A1 | 12/2010 | Schonherr et al. | |
| 2011/0017943 A1 | 1/2011 | Baus et al. | |

FOREIGN PATENT DOCUMENTS

| | | |
|---|---|---|
| DE | 4220225 A1 | 12/1993 |
| DE | 19942539 A1 | 3/2001 |
| DE | 102004025805 A1 | 12/2005 |
| DE | 102005007480 A1 | 9/2006 |
| EP | 0252561 A2 | 1/1988 |
| EP | 0470455 A2 | 2/1992 |
| EP | 0611824 A1 | 8/1994 |
| EP | 0662515 A1 | 7/1995 |
| EP | 0773296 A1 | 5/1997 |
| EP | 1010748 A1 | 6/2000 |
| EP | 1223219 A2 | 7/2002 |
| EP | 1252516 B1 | 10/2002 |
| FR | 2833490 A1 | 6/2003 |
| GB | 195876 A | 4/1923 |
| GB | 2235457 A | 3/1991 |
| JP | 60206893 | 10/1985 |
| JP | 06327481 | 11/1994 |
| JP | 07289261 | 11/1995 |
| JP | 08266281 | 10/1996 |
| WO | WO-9409094 A1 | 4/1994 |
| WO | WO-96/41882 A1 | 12/1996 |
| WO | WO-0023039 A2 | 4/2000 |
| WO | WO-00/58342 A1 | 10/2000 |
| WO | WO-0138476 A1 | 5/2001 |
| WO | WO-01/57528 A1 | 8/2001 |
| WO | WO-0157066 A2 | 8/2001 |
| WO | WO-0160916 A1 | 8/2001 |
| WO | WO-0220651 A2 | 3/2002 |
| WO | WO-0246342 A2 | 6/2002 |
| WO | WO-0246369 A2 | 6/2002 |
| WO | WO-03/010331 A2 | 2/2003 |
| WO | WO-03/018673 A1 | 3/2003 |
| WO | WO-03031500 A1 | 4/2003 |
| WO | WO-03/053383 A2 | 7/2003 |
| WO | WO-03/080137 A1 | 10/2003 |
| WO | WO-2004/000880 A1 | 12/2003 |
| WO | WO-2005033316 A2 | 4/2005 |
| WO | WO-2005068087 A2 | 7/2005 |
| WO | WO-2005115306 A2 | 12/2005 |
| WO | WO-2006082251 A2 | 8/2006 |
| WO | WO-2006082253 A2 | 8/2006 |
| WO | WO-2006103215 A1 | 10/2006 |
| WO | WO-2006103225 A1 | 10/2006 |
| WO | WO-2006103230 A1 | 10/2006 |
| WO | WO-2006103251 A1 | 10/2006 |
| WO | WO-2006103252 A2 | 10/2006 |
| WO | WO-2006103253 A2 | 10/2006 |
| WO | WO-2006131555 A1 | 12/2006 |
| WO | WO-2006131564 A2 | 12/2006 |
| WO | WO-2006136607 A2 | 12/2006 |
| WO | WO-2007006765 A1 | 1/2007 |
| WO | WO-2007014897 A1 | 2/2007 |
| WO | WO-2007042487 A2 | 4/2007 |

OTHER PUBLICATIONS

Hider, G.C., "A relatively simple test for the direct determination of the cysteine content in photographic gelatin using a thiol-specific fluorogenic reagent", The Imaging Science Journal, 1997, vol. 45, pp. 162-166.

Stringer, M. A., et al., "dewA Encodes a Fungal Hydrophobin Component of the *Asoergillus* Spore Wall", Molecular Microbiology, 1995, vol. 16, No. 1, pp. 33-44.

Belitsky, B. R., "Physical and Enzymological Interaction of *Bacillus subtilis* Proteins Required for De Novo Pyridoxal 5' Phosphate Biosynthesis", Journal of Bacteriology, 2004, vol. 186, No. 4, pp. 1191-1196.

Wösten, H. A. B., "Hydrophobins: Multipurpose Proteins", Annu. Rev. Microbial., 2001, vol. 55, pp. 625-646.

Janssen, M.I., et al., "Coating with Genetic Engineered Hydrophobin Promotes Growth of Fibroblasts on a Hydrophobic Solid, Biomaterials, 2002, vol. 23, pp. 4847-4854.

Ananichev, A.V., et al., "Immobilization of Glucose Isomerase by Adsorption on Porous Silochrome Under Vacuum", Prikladnaya Biokhimiya I Mikrobiologiya, 1984, vol. 20, No. 4, pp. 458-463.

Corvis, Y., et al., "Preparing catalytic surfaces for sensing applications by immobilizing enzymes via hydrophobin layers", Anal. Chem., 2005, vol. 77, pp. 1622-1630.

Scholtmeijer, K., et al., "Surface modifications created by using engineered hydrophobins", Applied and Environmental Microbiology, 2002, vol. 68, No. 3, pp. 1367-1373.

Scholtmeijer, K., et al., "Fungal hydrophobins in medical and technical applications" Applied Microbiology & Biotechnology, 2001, vol. 56, pp. 1-8.

Hektor, H. J., et al., "Hydrophobins: proteins with potential", Current Opinion in Biotechnology, 2005, vol. 16, pp. 434-439.

De Vocht, M. L., et al., "Structural and functional role of the disulfide bridges in the hydrophobin SC3", Journal of Biological Chemistry, 2000, vol. 275, No. 37, pp. 28428-28432.

Bauer, J. A., et al., "Three-dimensional structure of YaaE from *Bacillus subtilis*, a glutaminase implicated in pyridoxal-5'-phosphate biosynthesis", Journal of Biological Chemistry, 2004, vol. 279, No. 4, pp. 2704-2711.

Imai, Y., et al., "The Fission Yeast Mating Pheromone P-factor: its Molecular Structure, Gene Structure, and Ability to Induce Gene Expression and $G_1$ Arrest in the Mating Partner", Development, 1994, vol. 8, pp. 328-338.

Nakari-Setala, T., et al., "Expression of a Fungal Hydrophobin in the *Saccharomyces cerevisiae* Cell Wall: Effect on Cell Surface Properties and Immobilization", Applied and Environmental Microbiology, 2002, vol. 68, No. 7, pp. 3385-3391.

Linder, M., et al., "Surface Adhesion of Fusion Proteins Containing the Hydrophobins HFBI and HFBII from *Trichoderma reesei*", Protein Science, 2002, vol. 11, pp. 2257-2266.

\* cited by examiner

USE OF POLYPEPTIDES IN THE FORM OF ADHESIVE AGENTS

RELATED APPLICATIONS

This application is a national stage application under 35 U.S.C. §371 of PCT/EP2006/061085, filed Mar. 28, 2006, which claims priority to German application 10 2005 015 043.8, filed Mar. 31, 2005, and German application 10 2005 045 770.3, filed Sep. 23, 2005.

The invention relates to a multilayered composite or a coated substrate, comprising compounds of which at least 40% by weight are composed of alpha-amino acids linked via peptide bonds (referred to as polypeptide for short hereinbelow) as adhesion promoters between at least two adjacent layers of the composite or between the coating and the substrate. More specifically, the invention relates to the use of hydrophobins as adhesion promoters.

Hydrophobins are small proteins of from about 100 to 150 amino acids, which are characteristic for filamentous fungi, for example Schizophyllum commune. They most usually have 8 cysteine units.

Hydrophobins have a marked affinity for interfaces and are therefore suitable for coating surfaces. Thus it is possible to coat, for example, Teflon by means of hydrophobins to obtain a hydrophilic surface.

Hydrophobins may be isolated from natural substances. Our previous application, DE 10 2005 007 480.4, discloses a process for preparing hydrophobins.

The use of hydrophobins for various applications has been proposed in the prior art.

WO 96/41882 proposes the use of hydrophobins as emulsifiers, thickeners, surfactants, for hydrophilizing hydrophobic surfaces, for improving the water resistance of hydrophilic substrates, for preparing oil-in-water emulsions or water-in-oil emulsions. Pharmaceutical applications such as the preparation of ointments or creams and also cosmetic applications such as skin protection or the preparation of hair shampoos or hair rinses are also proposed.

EP 1 252 516 discloses the coating of windows, contact lenses, biosensors, medical apparatus, containers for carrying out experiments or for storage, ship hulls, solid particles or the chassis or bodywork of passenger vehicles with a hydrophobin-containing solution at a temperature from 30 to 80° C.

WO 03/53383 discloses the use of hydrophobin for treating keratin materials in cosmetic applications.

WO 03/10331 discloses a hydrophobin-coated sensor, for example a measuring electrode, to which further noncovalent substances, for example electroactive substances, antibodies or enzymes, have been attached.

Previously, very different adhesion promoters have been used for improving the adhesion of, for example, coatings to a large variety of substrates. Suitable are, according to Römpp Chemie Lexikon (1990 edition), for example, titanates, silanes, chromium complexes of unsaturated carboxylic acids. Specially mentioned adhesion promoters for adhesives are ethylene/acylamide copolymers, polymeric isocyanates or reactive organosilicon compounds.

Polyurethanes and polyethyleneimines are also known adhesion promoters.

The object of the present invention was to provide alternative adhesion promoters which have very good application properties and which effect, in particular, good adhesion of the individual layers of a multilayered composite or of a coating on a substrate.

Accordingly, the multilayered composite or the coated substrate, as defined at the outset, were found.

THE ADHESION PROMOTER

Figure 1:
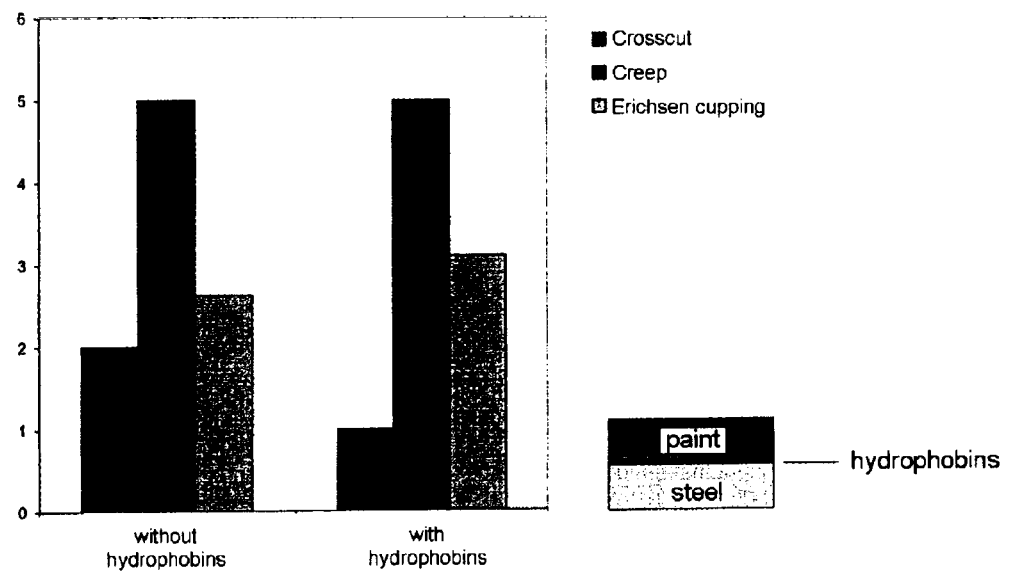
FIG. 1 shows the results of the performance tests using steel sheets as metallic substrates.

The multilayered composite or the coated substrate comprises the polypeptide defined at the outset as an adhesion promoter.

The polypeptide consists of at least 40% by weight, preferably at least 70% by weight, particularly preferably at least 90% by weight, and very particularly preferably at least 95 or 99% by weight, of alpha-amino acids linked via peptide bonds.

In a particular embodiment, the polypeptide consists exclusively of alpha-amino acids linked via peptide bonds.

Particularly suitable alpha-amino acids are glycine, alanine, valine, leucine, isoleucine, phenylalanine, tyrosine, proline, hydroxyproline, serine, threonine, cysteine, cystine, methionine, tryptophan, aspartic acid, glutamic acid, arginine, lysine and histidine.

The polypeptide preferably comprises the alpha-amino acid cysteine in a mixture with other alpha-amino acids.

The polypeptide particularly preferably consists of at least 0.1% by weight, particularly preferably at least 0.5, very particularly preferably at least 1% by weight, of cysteine. The cysteine content in the polypeptide generally does not exceed 15% by weight, in particular 10% by weight, and very particularly preferably does not exceed 7% by weight.

In a particular embodiment, the polypeptides are hydrophobins.

The term "hydrophobins" in accordance with the present invention means hereinbelow proteins of the general structural formula (I)

$$X_n\text{—}C^1\text{—}X_{1\text{-}50}\text{—}C^2\text{—}X_{0\text{-}5}\text{—}C^3\text{—}X_{1\text{-}100}\text{—}C^4\text{—}$$
$$X_{1\text{-}100}\text{—}C^5\text{—}X_{1\text{-}50}\text{—}C^6\text{—}X_{0\text{-}5}\text{—}C^7\text{—}X_{1\text{-}50}\text{—}$$
$$C^8\text{—}X_m \quad (I),$$

where X may be any of the 20 naturally occurring amino acids (Phe, Leu, Ser, Tyr, Cys, Trp, Pro, His, Gln, Arg, Ile, Met, Thr, Asn, Lys, Val, Ala, Asp, Glu, Gly). X may also in each case be identical or different. The indices next to X indicate in each case the number of amino acids, C is cysteine, alanine, serine, glycine, methionine or threonine, with at least four of the residues denoted C being cysteine, and the indices n and m are independently of one another natural numbers of 0 and 500, preferably from 15 to 300.

The polypeptides according to formula (I) are furthermore characterized by the property of their increasing, at room temperature, after coating of a glass surface, the contact angle of a water drop by at least 20°, preferably at least 25° and particularly preferably 30°, in each case compared to the contact angle of a water drop of similar size with the uncoated glass surface.

The amino acids denoted $C^1$ to $C^8$ are preferably cysteines; they may, however, also be replaced with other amino acids of similar spatial dimensions, preferably alanine, serine, threonine, methionine or glycine. However, at least four, preferably at least 5, particularly preferably at least 6 and in particular at least 7, of the positions $C^1$ to $C^8$ should consist of cysteines. Cysteines may either be in a reduced state or may form disulfide bridges between each other. Particular preference is given to the intramolecular formation of C—C bridges, in particular that with at least one, preferably 2, particularly preferably 3 and very particularly preferably 4, intramolecular disulfide bridges. The above-described substitution of cysteines by amino acids of similar spatial dimensions, involves advantageously substituting in pairs those C positions which can form intramolecular disulfide bridges between each other.

If cysteines, serines, alanines, glycines, methionines or threonines are also used in the positions indicated by X, the numbering of the individual C positions in the general formulae may change accordingly.

Preference is given to employing hydrophobins of the general formula (II)

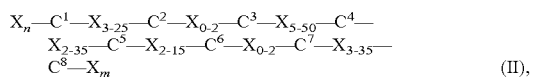

(II), to carry out the present invention, wherein X, C and the indices next to X and C are as defined above, but the indices n and m are numbers between 0 and 300 and the proteins are furthermore distinguished by the abovementioned contact angle change.

Particular preference is given to employing hydrophobins of the formula (III)

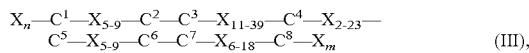

(III), wherein X, C and the indices next to X and C are as defined above, the indices n and m are numbers between 0 and 200 and the proteins are furthermore distinguished by the abovementioned contact angle change, and at least 6 of the residues denoted C are cysteines. Particular preference is given to all residues C being cysteines.

The residues $X_n$ and $X_m$ may be peptide sequences which are naturally linked to a hydrophobin. However, either or both residues may also be peptide sequences which are not naturally linked to a hydrophobin. This also includes those residues $X_n$ and/or $X_m$ in which a peptide sequence naturally occurring in a hydrophobin has been extended by a peptide sequence which does not naturally occur in a hydrophobin.

If $X_n$ and/or $X_m$ are peptide sequences which are not naturally linked to hydrophobins, such sequences are usually at least 20, preferably at least 35, particularly preferably at least 50 and very particularly preferably at least 100, amino acids in length. A residue of this kind which is not naturally linked to a hydrophobin will also be referred to as fusion partner hereinbelow. This is intended to express the fact that the proteins can consist of at least one hydrophobin part and one fusion partner which in nature do not occur together in this form.

The fusion partner may be selected from a multiplicity of proteins. It is also possible for a plurality of fusion partners to be linked to one hydrophobin part, for example to the amino terminus ($X_n$) and to the carboxy terminus ($X_m$) of said hydrophobin part. However, it is also possible to link, for example, two fusion partner parts to one position ($X_n$ or $X_m$) of the protein of the invention.

Particularly suitable fusion partner parts are proteins which occur naturally in microorganisms, in particular in *E. coli* or *Bacillus subtilis*. Examples of such fusion partner parts are the sequences yaad (SEQ ID NO:15 and 16), yaae (SEQ ID NO: 17 and 18), and thioredoxin. Fragments or derivatives of said sequences, which comprise only a part, preferably 70-99%, particularly preferably 80-98%, of said sequences or in which individual amino acids or nucleotides have been altered compared to the sequence mentioned, are also well suited, with the percentages given referring in each case to the number of amino acids.

It is furthermore also possible that the polypeptide sequence of the proteins used according to the invention has been modified, for example by glycosylation, acetylation or else by chemical crosslinking, for example with glutaraldehyde.

One characteristic of the proteins used according to the invention is the change in surface properties when the surfaces are coated with said proteins. The change in surface properties can be determined experimentally by measuring the contact angle of a water drop before and after coating of the surface with the protein and determining the difference of the two measurements.

The measurement of contact angles is known in principle to the skilled worker. The measurements are based on room temperature and water drops of 5 l. The precise experimental conditions for a method, suitable by way of example, of measuring the contact angle are illustrated in the experimental section. Under the conditions mentioned there, the proteins used according to the invention have the property of increasing the contact angle by at least 20°, preferably at least 25°, particularly preferably at least 30°, in each case compared to the contact angle of a water drop of similar size with the uncoated glass surface.

The positions of the polar and nonpolar amino acids in the hydrophobin part of the hydrophobins known to date are preserved, resulting in a characteristic hydrophobicity plot. Differences in biophysical properties and hydrophobicity resulted in the classification of the hydrophobins known to date into two classes, I and II (Wessels et al. 1994, Ann. Rev. Phytopathol., 32, 413-437).

The assembled membranes of class I hydrophobins are to a large extent insoluble (even to 1% sodium dodecyl sulfate (SDS) at an elevated temperature) and can only be dissociated again by means of concentrated trifluoroacetic acid (TFA) or formic acid. In contrast, the assembled forms of class II hydrophobins are less stable. They may be dissolved again even by 60% strength ethanol or 1% SDS (at room temperature).

Comparison of the amino acid sequences reveals that the length of the region between cysteine $C^3$ and $C^4$ is distinctly shorter in class II hydrophobins than in class I hydrophobins. Class II hydrophobins furthermore have more charged amino acids than class I.

Hydrophobins which are particularly preferred for carrying out the present invention are those of types dewA, rodA, hypA, hypB, sc3, basf1, basf2 which are structurally characterized in the sequence listing below. They may also be only parts or derivatives of said types. It is also possible to link a plurality of hydrophobin parts, preferably 2 or 3, of the same or a different structure to one another and to a corresponding suitable polypeptide sequence which is not naturally connected to a hydrophobin.

Particularly suitable for carrying out the present invention are furthermore the fusion proteins having the polypeptide sequences indicated in SEQ ID NO: 20, 22, 24 and also the nucleic acid sequences coding therefor, in particular the sequences according to SEQ ID NO: 19, 21, 23. Particularly preferred embodiments are also proteins which, starting from the polypeptide sequences indicated in SEQ ID NO. 20, 22 or 24, result from the substitution, insertion or deletion of at least one, up to 10, preferably 5, particularly preferably 5% of all, amino acids and which still have at least 50% of the biological property of the starting proteins. Biological property of the proteins here means the above-described increase in the contact angle by at least 20°.

The proteins used according to the invention can be prepared chemically by known processes of peptide synthesis, for example by solid phase synthesis according to Merrifield.

Naturally occurring hydrophobins can be isolated from natural sources by means of suitable methods. By way of example, reference is made to Wösten et. al., Eur. J Cell Bio. 63, 122-129 (1994) or WO 96/41882.

Fusion proteins may preferably be prepared by genetic engineering processes in which one nucleic acid sequence, in particular DNA sequence, coding for the fusion partner and one coding for the hydrophobin part are combined in such a way that the desired protein is generated by gene expression of the combined nucleic acid sequence in a host organism. A preparation process of this kind is disclosed in our previous application DE 102005007480.4.

Host organisms (producer organisms) which may be suitable here for the preparation process mentioned are prokaryotes (including Archaea) or eukaryotes, particularly bacteria including halobacteria and methanococci, fungi, insect cells, plant cells and mammalian cells, particularly preferably *Escherichia coli, Bacillus subtilis, Bacillus megaterium, Aspergillus oryzae, Aspergillus nidulans, Aspergillus niger, Pichia pastoris, Pseudomonas* spec., *lactobacilli, Hansenula polymorpha, Trichoderma reesei*, SF9 (or related cells), and others.

The invention moreover relates to the use of expression constructs comprising, under the genetic control of regulatory nucleic acid sequences, a nucleic acid sequence coding for a polypeptide used according to the invention and also to vectors comprising at least one of these expression constructs.

Constructs used preferably comprise a promoter 5' upstream of the particular coding sequence and a terminator sequence 3' downstream and, if appropriate, further customary regulatory elements, in each case operatively linked to the coding sequence.

An "operative linkage" means the sequential arrangement of promoter, coding sequence, terminator and, if appropriate, further regulatory elements in such a way that each of the regulatory elements is able to fulfill its function as required in expressing the coding sequence.

Examples of operatively linkable sequences are targeting sequences and also enhancers, polyadenylation signals and the like. Other regulatory elements comprise selectable markers, amplification signals, origins of replication and the like. Suitable regulatory sequences are described, for example, in Goeddel, Gene Expression Technology: Methods in Enzymology 185, Academic Press, San Diego, Calif. (1990).

In addition to these regulatory sequences, the natural regulation of these sequences may still be present upstream of the actual structural genes and, if appropriate, may have been genetically altered in such a way that the natural regulation has been switched off and expression of the genes has been increased.

A preferred nucleic acid construct also advantageously comprises one or more of the previously mentioned enhancer sequences which are functionally linked to the promoter and which enable expression of the nucleic acid sequence to be increased. Additional advantageous sequences such as further regulatory elements or terminators may also be inserted at the 3' end of the DNA sequences.

The nucleic acids may be present in the construct in one or more copies. The construct may also comprise additional markers such as antibiotic resistances or auxotrophy-complementing genes, if appropriate for the purpose of selecting said construct.

Regulatory sequences which are advantageous for the process are present, for example, in promoters such as the cos, tac, trp, tet, trp-tet, lpp, lac, lpp-lac, lacIq-T7, T5, T3, gal, trc, ara, rhaP (rhaPBAD)SP6, lambda-PR or in the lambda-P promoter, which promoters are advantageously used in Gram-negative bacteria. Further advantageous regulatory sequences are present, for example, in the Gram-positive promoters amy and SPO2, in the yeast or fungal promoters ADC1, MFalpha, AC, P-60, CYC1, GAPDH, TEF, rp28, ADH.

It is also possible to use artificial promoters for regulation.

For the purpose of expression in a host organism, the nucleic acid construct is advantageously inserted into a vector such as a plasmid or a phage, for example, which enables the genes to be expressed optimally in the host. Vectors mean, in addition to plasmids and phages, also any other vectors known to the skilled worker, i.e., for example, viruses such as SV40, CMV, baculovirus and adenovirus, transposons, IS elements, phasmids, cosmids, and linear or circular DNA, and also the *Agrobacterium* system.

These vectors may be replicated autonomously in the host organism or replicated chromosomally. These vectors constitute a further embodiment of the invention. Examples of suitable plasmids are, in *E. coli*, pLG338, pACYC184, pBR322, pUC18, pUC19, pKC30, pRep4, pHS1, pKK223-3, pDHE19.2, pHS2, pPLc236, pMBL24, pLG200, pUR290, pIN-III"3-B1, tgt11 or pBdCl, in *Streptomyces*, pIj101, pIJ364, pIJ702 or pIJ361, in *Bacillus*, pUB110, pC194 or pBD214, in *Corynebacterium* pSA77 or pAJ667, in fungi, pALS1, pIL2 or pBB116, in yeasts, 2alpha, pAG-1, YEp6, YEp13 or pEMBLYe23, or, in plants, pLGV23, pGHlac+, pBIN19, pAK2004 or pDH51. Said plasmids are a small selection of the possible plasmids. Other plasmids are well known to the skilled worker and can be found, for example, in the book Cloning Vectors (Eds. Pouwels P. H. et al., Elsevier, Amsterdam-New York-Oxford, 1985, ISBN 0 444 904018).

For the purpose of expressing the other genes which are present, the nucleic acid construct advantageously also comprises 3'-terminal and/or 5'-terminal regulatory sequences for increasing expression, which are selected for optimal expression in dependence on the host organism and the gene or genes selected.

These regulatory sequences are intended to enable the genes and protein expression to be specifically expressed. Depending on the host organism, this may mean, for example, that the gene is expressed or overexpressed only after induction or that it is expressed and/or overexpressed immediately.

In this connection, the regulatory sequences or factors may preferably influence positively and thereby increase expression of the genes which have been introduced. Thus, the regulatory elements may advantageously be enhanced at the level of transcription by using strong transcription signals such as promoters and/or enhancers. However, in addition to this, it is also possible to enhance translation by improving the stability of the mRNA, for example.

In a further embodiment of the vector, the vector which comprises the nucleic acid construct of the invention or the nucleic acid of the invention may also advantageously be introduced into the microorganisms in the form of a linear DNA and be integrated into the genome of the host organism by way of heterologous or homologous recombination. This linear DNA may consist of a linearized vector such as a plasmid or only of the nucleic acid construct or the nucleic acid.

In order to express heterologous genes optimally in organisms, it is advantageous to alter the nucleic acid sequences in accordance with the specific codon usage employed in the organism. The codon usage can readily be determined with the aid of computer analyses of other known genes of the organism in question.

An expression cassette is prepared by fusing a suitable promoter to a suitable coding nucleotide sequence and to a terminator signal or polyadenylation signal. Common recombination and cloning techniques, as are described, for example, in T. Maniatis, E. F. Fritsch and J. Sambrook, Molecular Cloning: A Laboratory Manual, Cold Spring Harbor Laboratory, Cold Spring Harbor, N.Y. (1989) and also in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987), are used for this purpose.

In order to achieve expression in a suitable host organism, the recombinant nucleic acid construct or gene construct is advantageously inserted into a host-specific vector which enables the genes to be expressed optimally in the host. Vectors are well known to the skilled worker and may be found, for example, in "Cloning Vectors" (Pouwels P. H. et al., Eds., Elsevier, Amsterdam-New York-Oxford, 1985).

It is possible to prepare, with the aid of the vectors, recombinant microorganisms which are, for example, transformed with at least one vector and which may be used for producing the proteins used according to the invention. Advantageously, the above-described recombinant constructs of the invention are introduced into a suitable host system and expressed. In this connection, familiar cloning and transfection methods known to the skilled worker, such as, for example, coprecipitation, protoplast fusion, electroporation, retroviral transfection and the like, are preferably used in order to cause said nucleic acids to be expressed in the particular expression system. Suitable systems are described, for example, in Current Protocols in Molecular Biology, F. Ausubel et al., Eds., Wiley Interscience, New York 1997, or Sambrook et al., Molecular Cloning: A Laboratory Manual. 2nd edition, Cold Spring Harbor Laboratory, Cold Spring Harbor Laboratory Press, Cold Spring Harbor, N.Y., 1989.

It is also possible to prepare homologously recombined microorganisms. For this purpose, a vector which comprises at least one section of a gene to be used according to the invention or of a coding sequence in which, if appropriate, at least one amino acid deletion, amino acid addition or amino acid substitution has been introduced in order to modify, for example functionally disrupt, the sequence (knockout vector), is prepared. The introduced sequence may, for example, also be a homolog from a related microorganism or be derived from a mammalian, yeast or insect source. Alternatively, the vector used for homologous recombination may be designed in such a way that the endogenous gene is, in the case of homologous recombination, mutated or otherwise altered but still encodes the functional protein (e.g. the upstream regulatory region may have been altered in such a way that expression of the endogenous protein is thereby altered). The altered section of the gene used according to the invention is in the homologous recombination vector. The construction of vectors which are suitable for homologous recombination is described, for example, in Thomas, K. R. and Capecchi, M. R. (1987) Cell 51:503.

Recombinant host organisms suitable for the nucleic acid used according to the invention or the nucleic acid construct are in principle any prokaryotic or eukaryotic organisms. Advantageously, microorganisms such as bacteria, fungi or yeasts are used as host organisms. Gram-positive or Gram-negative bacteria, preferably bacteria of the families Enterobacteriaceae, Pseudomonadaceae, Rhizobiaceae, Streptomycetaceae or Nocardiaceae, particularly preferably bacteria of the genera *Escherichia, Pseudomonas, Streptomyces, Nocardia, Burkholderia, Salmonella, Agrobacterium* or *Rhodococcus*, are advantageously used.

The organisms used in the process of preparing fusion proteins are, depending on the host organism, grown or cultured in a manner known to the skilled worker. Microorganisms are usually grown in a liquid medium which comprises a carbon source, usually in the form of sugars, a nitrogen source, usually in the form of organic nitrogen sources such as yeast extract or salts such as ammonium sulfate, trace elements such as iron salts, manganese salts and magnesium salts and, if appropriate, vitamins, at temperatures of between 0° C. and 100° C., preferably between 10° C. and 60° C., while being supplied with oxygen. In this connection, the pH of the nutrient liquid may or may not be kept at a fixed value, i.e. may or may not be regulated during cultivation. The cultivation may be carried out batchwise, semibatchwise or continuously. Nutrients may be initially introduced at the beginning of the fermentation or be fed in subsequently in a semicontinuous or continuous manner. The enzymes may be isolated from the organisms by the process described in the examples or be used for the reaction as a crude extract.

Proteins used according to the invention or functional, biologically active fragments thereof may be prepared by means of a recombinant process, with a protein-producing microorganism being cultured, expression of the proteins being induced if appropriate and said proteins being isolated from the culture. The proteins may also be produced in this way on an industrial scale if this is desired. The recombinant microorganism may be cultured and fermented by known methods. Bacteria may, for example, be propagated in TB medium or LB medium and at a temperature of from 20 to 40° C. and a pH of from 6 to 9. Suitable culturing conditions are described in detail, for example, in T. Maniatis, E. F. Fritsch and J. Sambrook, Molecular Cloning: A Laboratory Manual, Cold Spring Harbor Laboratory, Cold Spring Harbor, N.Y. (1989).

If the proteins used according to the invention are not secreted into the culture medium, the cells are then disrupted and the product is obtained from the lysate by known protein isolation processes. The cells may be disrupted, as desired, by means of high-frequency ultrasound, by means of high pressure, such as, for example, in a French pressure cell, by means of osmolysis, by the action of detergents, lytic enzymes or organic solvents, by means of homogenizers or by a combination of two or more of the processes listed.

The proteins used according to the invention may be purified using known chromatographic methods such as molecular sieve chromatography (gel filtration), for example Q Sepharose chromatography, ion exchange chromatography and hydrophobic chromatography, and also using other customary methods such as ultrafiltration, crystallization, salting-out, dialysis and native gel electrophoresis. Suitable processes are described, for example, in Cooper, F. G., Biochemische Arbeitsmethoden, Verlag Walter de Gruyter, Berlin, N.Y. or in Scopes, R., Protein Purification, Springer Verlag, New York, Heidelberg, Berlin.

It may be advantageous to isolate the recombinant protein by using vector systems or oligonucleotides which extend the cDNA by particular nucleotide sequences and thereby code for altered proteins or fusion proteins which are used, for example, to simplify purification. Examples of suitable modifications of this kind are "tags" acting as anchors, such as the modification known as the hexa-histidine anchor, or epitopes which can be recognized as antigens by antibodies (described, for example, in Harlow, E. and Lane, D., 1988, Antibodies: A Laboratory Manual. Cold Spring Harbor (N.Y.) Press). Other suitable tags are, for example, HA, calmodulin-BD, GST, MBD; chitin-BD, steptavidin-BD-avi-tag, Flag-tag, T7 etc. These anchors may be used for attaching the proteins to a solid support such as a polymer matrix, for example, which may, for example, be packed in a chromatography column, or may be used on a microtiter plate or on another support. The corresponding purification protocols can be obtained from the commercial affinity tag suppliers.

The proteins prepared as described may be used either directly as fusion proteins or, after cleaving off and removing the fusion partner, as "pure" hydrophobins.

If the fusion partner is intended to be removed, it is recommended to incorporate a potential cleavage site (specific recognition site for proteases) into the fusion protein between the hydrophobin part and the fusion partner part. Suitable cleavage sites are in particular those peptide sequences which otherwise occur neither in the hydrophobin part nor in the fusion partner part, which can be readily determined by means of bioinformatics tools. Particularly suitable are, for example, BrCN cleavage on methionine or protease-mediated cleavage with factor Xa, enterokinase cleavage, thrombin, TEV cleavage (tobacco etch virus protease).

Assignment of sequence names to DNA and polypeptide sequences in the sequence listing

| dewA DNA and polypeptide sequences | SEQ ID NO: 1 |
|---|---|
| dewA polypeptide sequence | SEQ ID NO: 2 |
| rodA DNA and polypeptide sequences | SEQ ID NO: 3 |
| rodA polypeptide sequence | SEQ ID NO: 4 |
| hypA DNA and polypeptide sequences | SEQ ID NO: 5 |
| hypA polypeptide sequence | SEQ ID NO: 6 |
| hypB DNA and polypeptide sequences | SEQ ID NO: 7 |
| hypB polypeptide sequence | SEQ ID NO: 8 |
| sc3 DNA and polypeptide sequences | SEQ ID NO: 9 |
| sc3 polypeptide sequence | SEQ ID NO: 10 |
| basf1 DNA and polypeptide sequences | SEQ ID NO: 11 |
| basf1 polypeptide sequence | SEQ ID NO: 12 |
| basf2 DNA and polypeptide sequences | SEQ ID NO: 13 |
| basf2 polypeptide sequence | SEQ ID NO: 14 |
| yaad DNA and polypeptide sequences | SEQ ID NO: 15 |
| yaad polypeptide sequence | SEQ ID NO: 16 |
| yaae DNA and polypeptide sequences | SEQ ID NO: 17 |
| yaae polypeptide sequence | SEQ ID NO: 18 |
| yaad-Xa-dewA-his DNA and polypeptide sequences | SEQ ID NO: 19 |
| yaad-Xa-dewA-his polypeptide sequence | SEQ ID NO: 20 |
| yaad-Xa-rodA-his DNA and polypeptide sequences | SEQ ID NO: 21 |
| yaad-Xa-rodA-his polypeptide sequence | SEQ ID NO: 22 |
| yaad-Xa-basf1-his DNA and polypeptide sequences | SEQ ID NO: 23 |
| yaad-Xa-basf1-his polypeptide sequence | SEQ ID NO: 24 |

The Multilayered Composite

Multilayered composites are employed for very different purposes, for example as packaging means (in particular composite films) or self-adhesive articles (multilayered composite of at least support and an adhesive layer).

The multilayered composites comprise at least two, preferably two to five, layers, it being possible for the individual layers to have a thickness of from 0.01 to 5 mm, for example. The individual layers may consist of natural or synthetic polymers or else of metal. The layers are in particular polymer films, paper, metal foils, metallized polymer films etc.

The above polypeptides are used as adhesion promoters between at least two adjacent layers of the multilayered composite. Preferably, at least one of the adjacent layers is a layer of a natural or synthetic polymer. Suitable polymers are in particular polycondensates such as polyesters, polyadducts such as polyurethanes, polyamides, polycarbonates or polyphenylene ethers or polyphenylene sulfides or polymers obtainable by free-radical or ionic polymerization of ethylenically unsaturated compounds (referred to as free-radical polymers for short). Such free-radical polymers consist preferably of at least 60% by weight, particularly preferably at least 80% by weight, of "main monomers" selected from C1 to C20 alkyl (meth)acrylates, vinyl esters of carboxylic acids comprising up to 20 carbon atoms, vinyl aromatics with up to 20 carbon atoms, ethylenically unsaturated nitriles, vinyl halides, vinyl ethers of alcohols comprising from 1 to 10 carbon atoms, aliphatic hydrocarbons with from 2 to 8 carbon atoms and one or two double bonds, in particular ethylene and propylene.

The polypeptides of the invention are suitable in particular also as adhesion promoters for nonpolar polymers; therefore, preferably at least one of the adjacent layers consists of a nonpolar polymer.

A measure of the polarity of polymers is the surface tension in air (21° C.). The lower the surface tension, the more nonpolar the polymer.

Therefore, at least one of the adjacent layers preferably consists of a nonpolar polymer having a surface tension of less than 50 mN/m (millinewton/meter), in particular less than 40 mN/m. Examples of nonpolar polymers of this kind are polyamide 66 (42.5 mN/m), polystyrene (43.5 mN/m), PVC (38.4 mN/m), polyethylene (36.1 mN/m), polypropylene (29 mN/m) or polytetrafluoroethane (22.5 mN/m).

Particular preference is given to both adjacent layers consisting of such a nonpolar polymer.

The amount of polypeptide required for adhesion promotion usually from 0.01 to 1000 mg (milligram/m$^2$ (square meter)), in particular 0.01 to 100 mg/m$^2$ and particularly preferably 0.1 to 10 mg/m$^2$.

The polypeptide may be applied to either of the two adjacent layers and, alternatively, may also be applied to both layers if both layers have already been preformed.

The polypeptide is preferably in the form of an aqueous solution; the polypeptide content of the solution is preferably from 0.01 to 5 parts by weight of polypeptide to 100 parts by weight of water. For the use according to the invention, the solution is preferably diluted further to a concentration of from 1 to 10 000 μg/ml of water, in particular 10 to 1000 μg/ml of water.

The application may therefore be followed first by a drying process in order to remove the water.

Subsequently, the two adjacent layers may be bonded by customary methods, for example by laminating.

The polypeptide may in particular also be applied to one of the adjacent layers (first layer), and the other adjacent layer (second layer) may then be prepared by applying a polymer dispersion, polymer solution or a solvent-free polymer to the first layer provided with the adhesion promoter and subsequently forming a film and/or thermal or photochemical curing. For this purpose, the polymer in particular is in the form of an aqueous dispersion or solution, particularly preferably an aqueous dispersion of an emulsion polymer, preferably of any of the free-radical polymers listed above. After the polymer has been applied, a drying process is then carried out, if appropriate.

The Coated Substrate

Substrates are coated for very different purposes. Mention should be made in particular of decorative coatings or protective coatings (generic term: coatings) or else adhesive coatings, it being possible for the adhesive to be applied as such to the substrate or to be bonded to it, for example, in the form of a self-adhesive article (label or adhesive tape).

The substrate, or the substrate surface, may consist of any material. Likewise, the coating or the substrate-facing surface of the coating may consist of any material.

Preferably, the substrate surface or the coating, or the substrate-facing surface of the coating, consists of natural or synthetic polymers.

Suitable polymers are in particular polycondensates such as polyesters, polyadducts such as polyurethanes, polyamides, polycarbonates or polyphenylene ethers or polyphenylene sulfides or polymers obtainable by free-radical or ionic polymerization of ethylenically unsaturated compounds (referred to as free-radical polymers for short).

With regard to the structure of the free-radical polymers and their main monomer content, the comments made above apply.

The polypeptides of the invention are suitable in particular also as adhesion promoters for nonpolar polymers; therefore at least the substrate surface or the substrate-facing surface of the coating preferably consists of a nonpolar polymer.

With respect to the contact angle as a measure for polarity, the comments made above likewise apply.

Particular preference is given to both the substrate surface and the substrate-facing surface of the coating consisting of such a nonpolar polymer.

The amount of polypeptide required for adhesion promotion corresponds to the amount indicated above.

The polypeptide may be applied to the substrate surface, to the substrate-facing surface of the coating or to both. Application to the substrate-facing surface of the coating is possible if said coating has been preformed, i.e. if a simple film or a multilayered composite (see above) is to be applied to the substrate.

The polypeptide is preferably in the form of an aqueous solution; the content of said solution is as indicated above.

It is therefore possible, after application, to carry out first a drying process in order to remove the water.

The coating may be applied to the substrate by customary methods; films or multilayered composites may, for example, be laminated on.

In particular, the coating may be prepared by applying a polymer dispersion, polymer solution or a solvent-free polymer to the substrate-facing surface provided with the adhesion promoter and by subsequently forming a film and/or thermal or photochemical curing. For this purpose, the polymer in particular is in the form of an aqueous dispersion or solution, particularly preferably an aqueous dispersion of an emulsion polymer, preferably of any of the free-radical polymers listed above. After the polymer has been applied, a drying process is then carried out, if appropriate.

The multilayered composites and coated substrates of the invention have a markedly increased strength. By using the polypeptides as adhesion promoters, adhesion of the coating to the substrate is stronger and adhesion of the individual layers of the multilayered composite to one another is superior.

In a further preferred embodiment of the invention, the substrate is a metal. In principle, this may be any metals. Examples include iron, steel, zinc, tin, aluminum, copper and alloys of said metals with themselves and with other metals. They may be, in particular, steel, steel coated with zinc, zinc alloys, aluminum or aluminum alloys. Particular preference is given to zinc or zinc alloys or substrates therewith, such as, for example, galvanized steel.

Zn or Al alloys are known to the skilled worker. The skilled worker selects the type and amount of alloy. components depending on the application purpose desired. Typical components of zinc alloys include in particular Al, Pb, Si, Mg, Sn, Cu or Cd. Typical components of aluminum alloys include in particular Mg, Mn, Si, Zn, Cr, Zr, Cu or Ti. The alloys may also be Al/Zn alloys which comprise approximately the same amount of Al and Zn. Steel coated with alloys of this kind is commercially available.

The metals may have any shape, with preference given, however, to metal foils, metal strips or metal sheets. The metal may also be a composite material with a metallic surface. It may be, for example, a composite of a polymer film and a metal.

The metallic surfaces will be coated with the polypeptides to be used according to the invention, preferably with hydrophobins, as adhesion promoters. This may be carried out using aqueous solutions of said polypeptides. Details of the coating process have already been mentioned above.

The coating may be in particular typical paints or paint systems for coating metallic surfaces. They may be paints cured thermally, photochemically or by other mechanisms.

Typical paints for coating metal surfaces comprise at least one binder and also crosslinkable components. The crosslinkable components may be crosslinkers which are employed in addition to a binder or they may be crosslinkable groups linked to the binder. The binder may of course also have crosslinkable groups and a crosslinker may be employed additionally. In this case, various possible combinations are conceivable. For example, binders and crosslinkers may be employed separately from one another. The binder in this case comprises reactive functional groups which can react with complementary, reactive functional groups in the crosslinkers. An alternative are self-crosslinking binders which comprise reactive functional groups capable of undergoing crosslinking reactions with groups of their kind ("with themselves") or with complementary, reactive functional groups on the same polymer. It is also possible for the crosslinkers exclusively to react with themselves.

Examples of suitable binders comprise (meth)acrylate (co) polymers, partially hydrolyzed polyvinyl esters, polyesters, alkyd resins, polylactones, polycarbonates, polyethers, epoxide resin-amine adducts, polyureas, polyamides, polyimides or polyurethanes. It is of course also possible to use mixtures of various polymers, provided that said mixture does not produce any undesired effects.

The crosslinking components may have thermally crosslinking groups or photochemically crosslinking groups. Examples of suitable thermal crosslinkers are crosslinkers based on epoxides, on melamine or on blocked isocyanates. Suitable crosslinkers for photochemical crosslinking are in particular compounds having multiple ethylenically unsaturated groups, in particular di- or polyfunctional acrylates.

The use according to the invention of polypeptides, preferably of hydrophobins, improves in an advantageous manner adhesion of the paint on the substrate. An improved resistance of the paint layer to creep in anticorrosion tests is also achieved.

The following examples are intended to illustrate the invention in more detail:

Part A) Preparation of Hydrophobins

Example 1

Preliminary Work for the Cloning of yaad-His$_6$/yaaE-His$_6$

A polymerase chain reaction was carried out with the aid of the oligonucleotides Hal570 and Hal571 (Hal 572/Hal 573).

The template DNA used was genomic DNA of the bacterium *Bacillus subtilis*. The PCR fragment obtained comprised the coding sequence of the *Bacillus subtilis* yaaD/yaaE gene and, at their termini, in each case an NcoI and, respectively, BglII restriction cleavage site. The PCR fragment was purified and cut with the restriction endonucleases NcoI and BglII. This DNA fragment was used as insert and cloned into the vector pQE60 from Qiagen, which had previously been linearized with the restriction endonucleases NcoI and BglII. The vectors thus obtained, pQE60YAAD#2/pQE60YaaE#5, may be used for expressing proteins consisting of YAAD::HIS$_6$ and YAAE::HIS$_6$, respectively.

```
                                           (SEQ ID NO: 25)
Hal570:    gcgcgcccatggctcaaacaggtactga (SEQ ID NO: 26)
Hal571:    gcagatctccagccgcgttcttgcatac (SEQ ID NO: 27)
Hal572:    ggccatgggattaacaataggtgtactagg (SEQ ID NO: 28)
Hal573:    gcagatcttacaagtgccttttgcttatattcc
```

Example 2

Cloning of yaad Hydrophobin DewA-His$_6$

A polymerase chain reaction was carried out with the oligonucleotide KaM 416 and KaM 417. The template DNA used was genomic DNA of the mold *Aspergillus nidulans*. The PCR fragment obtained comprised the coding sequence of the hydrophobin gene dewA and an N-terminal factor Xa proteinase cleavage site. The PCR fragment was purified and cut with the restriction endonuclease BamHI. This DNA fragment was used as insert and cloned into the pQE60YAAD#2 vector previously linearized with the restriction endonuclease BglII.

The vector thus obtained, #508, may be used for expressing a fusion protein consisting of YAAD::Xa::dewA::HIS$_6$.

```
                                           (SEQ ID NO: 29)
KaM416:  GCAGCCCATCAGGGATCCCTCAGCCTTGGTACCAGCGC (SEQ ID NO: 30)
KaM417:  CCCGTAGCTAGTGGATCCATTGAAGGCCGCATGAAGTTCTC
         CGTCTCCGC
```

Example 3

Cloning of yaad Hydrophobin RodA-His$_6$

The plasmid #513 was cloned analogously to plasmid #508, using the oligonucleotides KaM 434 and KaM 435.

```
                                           (SEQ ID NO: 31)
KaM434:  GCTAAGCGGATCCATTGAAGGCCGCATGAAGTTCTCCATTG
         CTGC (SEQ ID NO: 32)
KaM435:  CCAATGGGGATCCGAGGATGGAGCCAAGGG
```

Example 4

Cloning of yaad Hydrophobin BASF1-His$_6$

The plasmid #507 was cloned analogously to plasmid #508, using the oligonucleotides KaM 417 and KaM 418. The template DNA employed was an artificially synthesized DNA sequence—hydrophobin BASF1—(see appendix).

```
                                           (SEQ ID NO: 30)
KaM417:  CCCGTAGCTAGTGGATCCATTGAAGGCCGCATGAAGTTCTC
         CGTCTCCGC (SEQ ID NO: 33)
KaM418:  CTGCCATTCAGGGGATCCCATATGGAGGAGGGAGACAG
```

Example 5

Cloning of the yaad Hydrophobin BASF2-His$_6$

The plasmid #506 was cloned analogously to plasmid #508, using the oligonucleotides KaM 417 and KaM 418. The template DNA employed was an artificially synthesized DNA sequence—hydrophobin BASF2 (see appendix).

```
                                           (SEQ ID NO: 30)
KaM417:  CCCGTAGCTAGTGGATCCATTGAAGGCCGCATGAAGTTCTC
         CGTCTCCGC (SEQ ID NO: 33)
KaM418:  CTGCCATTCAGGGGATCCCATATGGAGGAGGGAGACAG
```

Example 6

Cloning of the yaad Hydrophobin SC3-His$_6$

The plasmid #526 was cloned analogously to plasmid #508, using the oligonucleotides KaM464 and KaM465. The template DNA employed was *Schyzophyllum commune* cDNA (see appendix).

```
                                           (SEQ ID NO: 34)
KaM464:        CGTTAAGGATCCGAGGATGTTGATGGGGGTGC (SEQ ID NO: 35)
KaM465:        GCTAACAGATCTATGTTCGCCCGTCTCCCCGTCGT
```

Example 7

Fermentation of the Recombinant *E. coli* Strain yaad Hydrophobin DewA-His$_6$

Inoculation of 3 ml of LB liquid medium with an *E. coli* strain expressing yaad hydrophobin DewA-His$_6$ in 15 ml Greiner tubes. Incubation at 37° C. on a shaker at 200 rpm at 37° C. for 8 h. In each case 2 1 l Erlenmeyer flasks with baffles and 250 ml of LB medium (+100 μg/ml ampicillin) are inoculated with 1 ml of preculture and incubated on a shaker at 180 rpm at 37° C. for 9 h. Inoculate 13.5 l of LM medium (+100 μg/mi ampicillin) with 0.5 l of preculture (OD$_{600\ nm}$ 1:10 measured against H$_2$O) in a 20 l fermenter. Addition of 140 ml of 100 mM IPTG at an OD$_{60\ nm}$ of ~3.5. After 3 h, cool fermenter to 10° C. and remove fermentation broth by centrifugation. Use cell pellet for further purification.

Example 8

Purification of the Recombinant Hydrophobin Fusion Protein (Purification of Hydrophobin Fusion Proteins Possessing a C-Terminal His6 Tag)

100 g of cell pellet (100-500 mg of hydrophobin) are made up with 50 mM sodium phosphate buffer, pH 7.5, to a total volume of 200 ml and resuspended. The suspension is treated with an Ultraturrax type T25 (Janke and Kunkel; IKA-Labortechnik) for 10 minutes and subsequently, for the purposes of degrading the nucleic acids, incubated with 500 units of benzonase (Merck, Darmstadt; order No. 1.01697.0001) at room temperature for 1 hour. Prior to cell disruption, a filtration is carried out using a glass cartridge (P1). For the purposes of disrupting the cells and of shearing of the remaining genomic DNA, two homogenizer runs are carried out at 1500 bar (Microfluidizer M-110EH; Microfluidics Corp.). The homogenate is centrifuged (Sorvall RC-5B, GSA Rotor, 250 ml centrifuge beaker, 60 minutes, 4° C., 12 000 rpm, 23 000 g), the supernatant is put on ice and the pellet is resuspended in 100 ml of sodium phosphate buffer, pH 7.5. Centrifugation and resuspension are repeated three times, the sodium phosphate buffer comprising 1% SDS at the third repeat. After resuspension, the solution is stirred for one hour, followed by a final centrifugation (Sorvall RC-5B, GSA Rotor, 250 ml centrifuge beaker, 60 minutes, 4° C., 12 000 rpm, 23 000 g). According to SDS-PAGE analysis, the hydrophobin is present in the supernatant after the final centrifugation. The experiments show that hydrophobin is present in the corresponding E. coli cells probably in the form of inclusion bodies. 50 ml of the hydrophobin-comprising supernatant are applied to a 50 ml nickel-Sepharose High Performance 17-5268-02 column (Amersham) equilibrated with 50 mM Tris-Cl buffer, pH 8.0. The column is washed with 50 mM Tris-Cl buffer, pH 8.0, and the hydrophobin is subsequently eluted with 50 mM Tris-Cl buffer, pH 8.0, comprising 200 mM imidazole. For the purpose of removing the imidazole, the solution is dialyzed against 50 mM Tris-Cl buffer, pH 8.0.

The hydrophobin has a molecular weight of approx. 53 kD. Some of the smaller bands represent degradation products of hydrophobin.

Example 9

Performance Testing; Characterization of the Hydrophobin by Changing the Contact Angle of a Water Droplet on Glass Substrate:

Glass (window glass, Süddeutsche Glas, Mannheim, Germany):

Hydrophobin concentration: 100 μg/mL

Incubation of glass slides overnight (temperature 80° C.) in 50 mM sodium acetate pH 4+0.1% Tween 20 followed by coating, washing in distilled water followed by incubation: 10 min/80° C./1% SDS solution in dist. water washing in dist. water The samples are dried in air and the contact angle (in degrees) of a droplet of 5 μl of water is determined.

The contact angle was measured on a Dataphysics Contact Angle System OCA 15+ instrument, software SCA 20.2.0. (November 2002). The measurement was carried out according to the manufacturer's instructions.

Untreated glass resulted in a contact angle of 30±5°; a coating with the functional hydrophobin according to Example 8 (yaad-dewA-his$_6$) resulted in contact angles of 75±5°.

Part B) the Use of Polypeptides as Adhesion Promoters

Example 10

Polyethylene Substrate

Materials Used:
Solution Used:
A solution of the fusion protein prepared according to Example 8, yaad-Xa-dewA-his (SEQ ID NO: 19), in water was employed in the performance experiments. Hydrophobin concentration in solution: 100 μg/ml (0.01% by weight).
Substrate: Shaped Bodies (Small Plates) of Polyethylene
Coating:
A polyester film was coated with Acronal A 240, a commercial, aqueous polyacrylate dispersion from BASF for pressure-sensitive adhesives, and dried and cut into strips of 2.5 cm in width. The adhesive strips obtained were used for coating the PE platelets.
Procedure:
The polypeptide solution was applied to polyethylene plates and dried (pretreated polyethylene plates).
Subsequently, adhesive strips were bonded to pretreated and, for comparison, to untreated polyethylene plates and the force necessary to remove the adhesive strips was determined (peel strength in N)
Peel strength with polypeptide as adhesion promoter: 4.7 N
Peel strength without polypeptide as adhesion promoter: 2.6 N Example 11

Metallic Substrates

A solution of the fusion protein prepared according to Example 8, yaad-Xa-dewA-his (SEQ ID NO: 19), in water was employed in the performance experiments. Hydrophobin concentration in solution: 100 μg/ml (0.01% by weight).

The following test sheets were used as metallic substrates:

| No. | Substrate |
| --- | --- |
| Example 11-1 | Steel (type ST 2 (materials No. 1.0330)) |
| Example 11-2 | Galvanized steel (sendzimir-galvanized steel sheets GARDOBOND OE HDG/2 (Chemetall)) |
| Example 11-3 | Aluminum (AlMgSi AA 6016 GARDOBOND untreated (Chemetall)) |

The paint used was a baked topcoat based on alkyd melamine.

Experimental Description

The aluminum sheets were pickled in an alkaline cleaning dipping bath (60 g/l NaOH, 60° C., 1 min) and rinsed with distilled water. The sheets were then descaled in an acidic descaling bath with HNO$_3$/H2O (1:1) at room temperature for 15 seconds, rinsed with distilled water and blown dry with pressurized air.

The galvanized steel sheets and the steel sheets were rinsed with hot river water, subsequently rinsed with distilled water and blown dry with pressurized air.

The sheets were coated with the hydrophobins by dipping the former into the abovementioned solution, in each case at room temperature. The aluminum sheets were dipped for 16 h, the galvanized steel sheets and the steel sheets were dipped for 4 h. The sheets were subsequently rinsed with distilled water and blown dry with pressurized air.

After coating with the hydrophobin as adhesion promoter, the sheets were dipped into a baked topcoat based on alkyd melamine in a plastic bowl for 15 s and predried in air for approx. 1 h. This was followed by drying in a drying oven at 190° C. for 30 min and curing.

For comparison, in each case a further sample was prepared in the same manner with the paint but without the hydrophobin adhesion promoter.

Performance Test

The performance of the sheets was assessed by EN ISO 2409 (crosscut), EN ISO 4628-8 (creep) and DIN 53156 (Erichsen cupping).

The crosscut test assesses the appearance of the paint surface on the basis of predefined standards, after a crosscut has been cut into said surface. This involves evaluating the extent to which the paint flakes off the surface due to making the crosscut. The evaluation is done in the known manner with the aid of grades from 0 to 5, with 0 being the best and 5 the worst score.

The creep of the paint layer is determined by a standard corrosion test (exposure in the salt spray chamber (SS DIN 50021)) of the sheets. The creep of the aluminum sheets was evaluated after 298 h, that of the steel sheets was evaluated after 50 h and that of the galvanized steel sheets was evaluated after 190 h, in each case on the basis of predefined standards and using grades from 0 to 5, with 0 being the best and 5 being the worst score.

The Erichsen cupping comprises pressing a ball against the back of the sample and making a depression. The appearance of the paint at the mark is evaluated on the basis of predefined standards, with in this case 5 being the best and 0 being the worst score.

The results of the performance tests are summarized below.

Example 11-1

Steel Substrate

As shown in FIG. 1, using a hydrophobin as adhesion promoter does not change the creep (grade 5) compared with a sample without hydrophobin. The crosscut test (lower value) and the Erichsen cupping test (higher value) in each case give a superior result.

Example 11-2

Galvanized Steel Substrate

Figure 2:
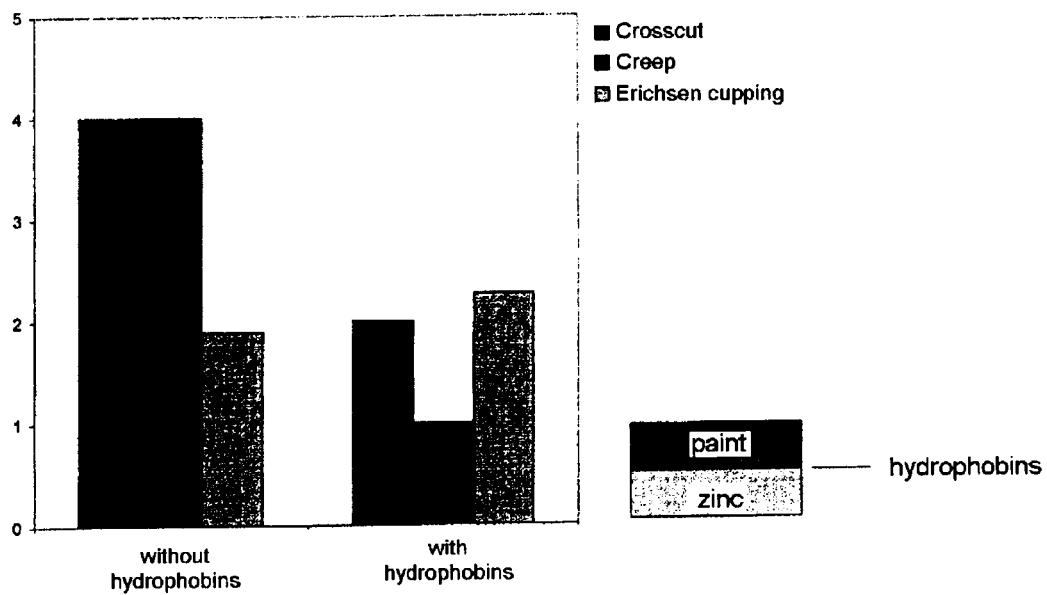
FIG. 2 shows the results of the performance tests using Galvanized steel sheets as metallic substrates.

As shown in FIG. 2, using hydrophobins as adhesion promoters on galvanized steel produces values which are in all three cases superior to those without adhesion promoter (lower values for crosscut and creep and higher value for Erichsen cupping). The clearest improvement is achieved in corrosion protection integrity (creep) (grade 1 with adhesion promoter, in contrast to grade 4 without adhesion promoter).

Example 11-3

Aluminum Substrate

Figure 3:
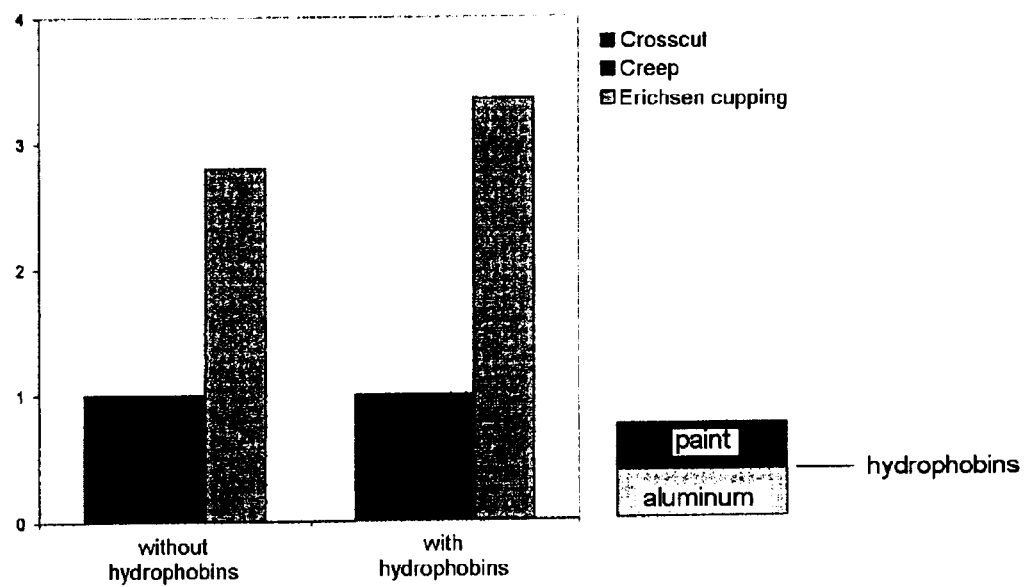
FIG. 3 shows the results of the performance tests using aluminum sheets as metallic substrates.

As shown in FIG. 3, in the case of an aluminum substrate, crosscut and creep are good even without adhesion promoter. The Erichsen cupping results in a slight improvement still.

We claim:

1. A coated metallic substrate comprising a compound between the coating and the substrate, wherein at least 40% by weight of the compound consists of a polypeptide as an adhesion promoter between the coating and the substrate, wherein the polypeptide is a hydrophobin of the formula $$X_n - C^1 - X_{5-9} - C^2 - C^3 - X_{11-39} - C^4 - X_{2-23} - C^5 - X_{5-9} - C^6 - C^7 - X_{6-18} - C^8 - X_m \quad (III),$$

wherein each amino acid residue of each X independently is a naturally occurring amino acid Phe, Leu, Ser, Tyr, Cys, Trp, Pro, His, Gln, Arg, Ile, Met, Thr, Asn, Lys, Val, Ala, Asp, Glu, Gly; each numerical subscript designates the number of amino acid residues of its adjacent X; subscripts n and m independently designate the number of amino acids from 0 to 500, inclusive, of its adjacent X; and each C independently is Cys, Ala, Ser, Gly, Met or Thr, provided that at least seven of the C residues are Cys, wherein said polypeptide has a property in increasing the contact angle of a water drop on a glass surface coated with said polypeptide by at least 20° as compared to the contact angle of a water drop of similar size on an uncoated glass surface as measured at room temperature, and wherein the substrate comprises steel, steel coated with zinc, zinc alloys, aluminum or aluminum alloys.

2. The coated metallic substrate of claim 1, wherein in the formula (III) the subscripts n and m independently designate the number of amino acids from 15 to 300, inclusive, of the X adjacent each n and m.

3. The coated metallic substrate of claim 1, wherein the coating comprises a paint layer.

4. The coated metallic substrate of claim 1, wherein the substrate-facing surface of the coating consists of a natural or synthetic polymer.

5. The coated metallic substrate of claim 1, wherein the substrate consists of galvanized steel.

6. The coated metallic substrate of claim 1, wherein the polypeptide improves adhesion of the coating and the substrate.

7. A process for preparing the coated metallic substrate of claim 1, comprising:
  applying the polypeptide to the substrate as an aqueous solution,
  performing a drying procedure, and
  applying the coating to the polypeptide-treated substrate.

8. The process of claim 7, wherein the coating is applied as an aqueous solution or dispersion, and the drying procedure is performed after application of the coating.

9. The process of claim 8, wherein the aqueous solution or dispersion is an aqueous dispersion of an emulsion polymer.

10. A process for preparing the coated metallic substrate of claim 1, comprising:
  applying the polypeptide to a surface of the substrate or a substrate-facing surface of a coating agent,
  performing a drying procedure if the polypeptide is applied as an aqueous solution, and
  subsequently applying the coating agent to the substrate.

11. A process for preparing the coated metallic substrate of claim 1, comprising:
  applying the polypeptide to a surface of the substrate,
  performing a drying procedure if the polypeptide is applied as an aqueous solution, and
  preparing the coating by forming a film of a natural or synthetic polymer on the substrate surface.

12. The process of claim 11, wherein the natural or synthetic polymer is in form of an aqueous solution or dispersion, and a drying procedure is carried out after formation of the film.

13. The process of claim 12, wherein the aqueous solution or dispersion is an aqueous dispersion of an emulsion polymer.

14. The process of claim 7, wherein the coating is a paint.

* * * * *

SEQUENCE LISTING

```
<160> NUMBER OF SEQ ID NOS: 35

<210> SEQ ID NO 1
<211> LENGTH: 405
<212> TYPE: DNA
<213> ORGANISM: Unknown
<220> FEATURE:
<221> NAME/KEY: CDS
<222> LOCATION: (1)..(405)
<223> OTHER INFORMATION: basf-dewA

<400> SEQUENCE: 1 atg cgc ttc atc gtc tct ctc ctc gcc ttc act gcc gcg gcc acc gcg      48
Met Arg Phe Ile Val Ser Leu Leu Ala Phe Thr Ala Ala Ala Thr Ala
1               5                   10                  15 acc gcc ctc ccg gcc tct gcc gca aag aac gcg aag ctg gcc acc tcg      96
Thr Ala Leu Pro Ala Ser Ala Ala Lys Asn Ala Lys Leu Ala Thr Ser
                20                  25                  30 gcg gcc ttc gcc aag cag gct gaa ggc acc acc tgc aat gtc ggc tcg     144
Ala Ala Phe Ala Lys Gln Ala Glu Gly Thr Thr Cys Asn Val Gly Ser
            35                  40                  45 atc gct tgc tgc aac tcc ccc gct gag acc aac aac gac agt ctg ttg     192
Ile Ala Cys Cys Asn Ser Pro Ala Glu Thr Asn Asn Asp Ser Leu Leu
        50                  55                  60 agc ggt ctg ctc ggt gct ggc ctt ctc aac ggg ctc tcg ggc aac act     240
Ser Gly Leu Leu Gly Ala Gly Leu Leu Asn Gly Leu Ser Gly Asn Thr
65                  70                  75                  80 ggc agc gcc tgc gcc aag gcg agc ttg att gac cag ctg ggt ctg ctc     288
Gly Ser Ala Cys Ala Lys Ala Ser Leu Ile Asp Gln Leu Gly Leu Leu
```

```
            85                  90                  95
gct ctc gtc gac cac act gag gaa ggc ccc gtc tgc aag aac atc gtc    336
Ala Leu Val Asp His Thr Glu Glu Gly Pro Val Cys Lys Asn Ile Val
        100                 105                 110 gct tgc tgc cct gag gga acc acc aac tgt gtt gcc gtc gac aac gct    384
Ala Cys Cys Pro Glu Gly Thr Thr Asn Cys Val Ala Val Asp Asn Ala
            115                 120                 125 ggc gct ggt acc aag gct gag                                         405
Gly Ala Gly Thr Lys Ala Glu
    130                 135

<210> SEQ ID NO 2
<211> LENGTH: 135
<212> TYPE: PRT
<213> ORGANISM: Unknown
<220> FEATURE:
<223> OTHER INFORMATION: basf-dewA

<400> SEQUENCE: 2

Met Arg Phe Ile Val Ser Leu Leu Ala Phe Thr Ala Ala Thr Ala
1               5                   10                  15

Thr Ala Leu Pro Ala Ser Ala Ala Lys Asn Ala Lys Leu Ala Thr Ser
            20                  25                  30

Ala Ala Phe Ala Lys Gln Ala Glu Gly Thr Thr Cys Asn Val Gly Ser
        35                  40                  45

Ile Ala Cys Cys Asn Ser Pro Ala Glu Thr Asn Asn Asp Ser Leu Leu
    50                  55                  60

Ser Gly Leu Leu Gly Ala Gly Leu Leu Asn Gly Leu Ser Gly Asn Thr
65                  70                  75                  80

Gly Ser Ala Cys Ala Lys Ala Ser Leu Ile Asp Gln Leu Gly Leu Leu
                85                  90                  95

Ala Leu Val Asp His Thr Glu Glu Gly Pro Val Cys Lys Asn Ile Val
            100                 105                 110

Ala Cys Cys Pro Glu Gly Thr Thr Asn Cys Val Ala Val Asp Asn Ala
        115                 120                 125

Gly Ala Gly Thr Lys Ala Glu
    130                 135

<210> SEQ ID NO 3
<211> LENGTH: 471
<212> TYPE: DNA
<213> ORGANISM: Unknown
<220> FEATURE:
<221> NAME/KEY: CDS
<222> LOCATION: (1)..(471)
<223> OTHER INFORMATION: basf-rodA

<400> SEQUENCE: 3 atg aag ttc tcc att gct gcc gct gtc gtt gct ttc gcc gcc tcc gtc    48
Met Lys Phe Ser Ile Ala Ala Ala Val Val Ala Phe Ala Ala Ser Val
1               5                   10                  15 gcg gcc ctc cct cct gcc cat gat tcc cag ttc gct ggc aat ggt gtt    96
Ala Ala Leu Pro Pro Ala His Asp Ser Gln Phe Ala Gly Asn Gly Val
            20                  25                  30 ggc aac aag ggc aac agc aac gtc aag ttc cct gtc ccc gaa aac gtg   144
Gly Asn Lys Gly Asn Ser Asn Val Lys Phe Pro Val Pro Glu Asn Val
        35                  40                  45 acc gtc aag cag gcc tcc gac aag tgc ggt gac cag gcc cag ctc tct   192
Thr Val Lys Gln Ala Ser Asp Lys Cys Gly Asp Gln Ala Gln Leu Ser
    50                  55                  60
```

| | | | | | | | | | | | | | | | | |
|---|---|---|---|---|---|---|---|---|---|---|---|---|---|---|---|---|
| tgc | tgc | aac | aag | gcc | acg | tac | gcc | ggt | gac | acc | aca | acc | gtt | gat | gag | 240 |
| Cys | Cys | Asn | Lys | Ala | Thr | Tyr | Ala | Gly | Asp | Thr | Thr | Thr | Val | Asp | Glu | |
| 65 | | | | 70 | | | | | 75 | | | | | | 80 | |
| ggt | ctt | ctg | tct | ggt | gcc | ctc | agc | ggc | ctc | atc | ggc | gcc | ggg | tct | ggt | 288 |
| Gly | Leu | Leu | Ser | Gly | Ala | Leu | Ser | Gly | Leu | Ile | Gly | Ala | Gly | Ser | Gly | |
| | | | | 85 | | | | | 90 | | | | | 95 | | |
| gcc | gaa | ggt | ctt | ggt | ctc | ttc | gat | cag | tgc | tcc | aag | ctt | gat | gtt | gct | 336 |
| Ala | Glu | Gly | Leu | Gly | Leu | Phe | Asp | Gln | Cys | Ser | Lys | Leu | Asp | Val | Ala | |
| | | | 100 | | | | | 105 | | | | | 110 | | | |
| gtc | ctc | att | ggc | atc | caa | gat | ctt | gtc | aac | cag | aag | tgc | aag | caa | aac | 384 |
| Val | Leu | Ile | Gly | Ile | Gln | Asp | Leu | Val | Asn | Gln | Lys | Cys | Lys | Gln | Asn | |
| | | | 115 | | | | | 120 | | | | | 125 | | | |
| att | gcc | tgc | tgc | cag | aac | tcc | ccc | tcc | agc | gcg | gat | ggc | aac | ctt | att | 432 |
| Ile | Ala | Cys | Cys | Gln | Asn | Ser | Pro | Ser | Ser | Ala | Asp | Gly | Asn | Leu | Ile | |
| | 130 | | | | | 135 | | | | | 140 | | | | | |
| ggt | gtc | ggt | ctc | cct | tgc | gtt | gcc | ctt | ggc | tcc | atc | ctc | | | | 471 |
| Gly | Val | Gly | Leu | Pro | Cys | Val | Ala | Leu | Gly | Ser | Ile | Leu | | | | |
| 145 | | | | 150 | | | | | 155 | | | | | | | |

<210> SEQ ID NO 4
<211> LENGTH: 157
<212> TYPE: PRT
<213> ORGANISM: Unknown
<220> FEATURE:
<223> OTHER INFORMATION: basf-rodA

<400> SEQUENCE: 4

Met Lys Phe Ser Ile Ala Ala Val Val Ala Phe Ala Ala Ser Val
1               5                   10                  15

Ala Ala Leu Pro Pro Ala His Asp Ser Gln Phe Ala Gly Asn Gly Val
            20                  25                  30

Gly Asn Lys Gly Asn Ser Asn Val Lys Phe Pro Val Pro Glu Asn Val
        35                  40                  45

Thr Val Lys Gln Ala Ser Asp Lys Cys Gly Asp Gln Ala Gln Leu Ser
    50                  55                  60

Cys Cys Asn Lys Ala Thr Tyr Ala Gly Asp Thr Thr Thr Val Asp Glu
65              70                  75                  80

Gly Leu Leu Ser Gly Ala Leu Ser Gly Leu Ile Gly Ala Gly Ser Gly
                85                  90                  95

Ala Glu Gly Leu Gly Leu Phe Asp Gln Cys Ser Lys Leu Asp Val Ala
            100                 105                 110

Val Leu Ile Gly Ile Gln Asp Leu Val Asn Gln Lys Cys Lys Gln Asn
        115                 120                 125

Ile Ala Cys Cys Gln Asn Ser Pro Ser Ser Ala Asp Gly Asn Leu Ile
    130                 135                 140

Gly Val Gly Leu Pro Cys Val Ala Leu Gly Ser Ile Leu
145                 150                 155

<210> SEQ ID NO 5
<211> LENGTH: 336
<212> TYPE: DNA
<213> ORGANISM: Unknown
<220> FEATURE:
<221> NAME/KEY: CDS
<222> LOCATION: (1)..(336)
<223> OTHER INFORMATION: basf-HypA

<400> SEQUENCE: 5

| | | | | | | | | | | | | | | | | |
|---|---|---|---|---|---|---|---|---|---|---|---|---|---|---|---|---|
| atg | atc | tct | cgc | gtc | ctt | gtc | gct | gct | ctc | gtc | gct | ctc | ccc | gct | ctt | 48 |
| Met | Ile | Ser | Arg | Val | Leu | Val | Ala | Ala | Leu | Val | Ala | Leu | Pro | Ala | Leu | |
| 1 | | | | 5 | | | | | 10 | | | | | 15 | | |

```
gtt act gca act cct gct ccc gga aag cct aaa gcc agc agt cag tgc      96
Val Thr Ala Thr Pro Ala Pro Gly Lys Pro Lys Ala Ser Ser Gln Cys
         20                  25                  30 gac gtc ggt gaa atc cat tgc tgt gac act cag cag act ccc gac cac     144
Asp Val Gly Glu Ile His Cys Cys Asp Thr Gln Gln Thr Pro Asp His
             35                  40                  45 acc agc gcc gcc gcg tct ggt ttg ctt ggt gtt ccc atc aac ctt ggt     192
Thr Ser Ala Ala Ala Ser Gly Leu Leu Gly Val Pro Ile Asn Leu Gly
 50                  55                  60 gct ttc ctc ggt ttc gac tgt acc ccc att tcc gtc ctt ggc gtc ggt     240
Ala Phe Leu Gly Phe Asp Cys Thr Pro Ile Ser Val Leu Gly Val Gly
 65                  70                  75                  80 ggc aac aac tgt gct gct cag cct gtc tgc tgc aca gga aat caa ttc     288
Gly Asn Asn Cys Ala Ala Gln Pro Val Cys Cys Thr Gly Asn Gln Phe
                 85                  90                  95 acc gca ttg att aac gct ctt gac tgc tct cct gtc aat gtc aac ctc     336
Thr Ala Leu Ile Asn Ala Leu Asp Cys Ser Pro Val Asn Val Asn Leu
            100                 105                 110
```

<210> SEQ ID NO 6
<211> LENGTH: 112
<212> TYPE: PRT
<213> ORGANISM: Unknown
<220> FEATURE:
<223> OTHER INFORMATION: basf-HypA

<400> SEQUENCE: 6

```
Met Ile Ser Arg Val Leu Val Ala Ala Leu Val Ala Leu Pro Ala Leu
 1               5                  10                  15

Val Thr Ala Thr Pro Ala Pro Gly Lys Pro Lys Ala Ser Ser Gln Cys
             20                  25                  30

Asp Val Gly Glu Ile His Cys Cys Asp Thr Gln Gln Thr Pro Asp His
         35                  40                  45

Thr Ser Ala Ala Ala Ser Gly Leu Leu Gly Val Pro Ile Asn Leu Gly
 50                  55                  60

Ala Phe Leu Gly Phe Asp Cys Thr Pro Ile Ser Val Leu Gly Val Gly
 65                  70                  75                  80

Gly Asn Asn Cys Ala Ala Gln Pro Val Cys Cys Thr Gly Asn Gln Phe
                 85                  90                  95

Thr Ala Leu Ile Asn Ala Leu Asp Cys Ser Pro Val Asn Val Asn Leu
            100                 105                 110
```

<210> SEQ ID NO 7
<211> LENGTH: 357
<212> TYPE: DNA
<213> ORGANISM: Unknown
<220> FEATURE:
<221> NAME/KEY: CDS
<222> LOCATION: (1)..(357)
<223> OTHER INFORMATION: basf-HypB

<400> SEQUENCE: 7

```
atg gtc agc acg ttc atc act gtc gca aag acc ctt ctc gtc gcg ctc      48
Met Val Ser Thr Phe Ile Thr Val Ala Lys Thr Leu Leu Val Ala Leu
 1               5                  10                  15 ctc ttc gtc aat atc aat atc gtc gtt ggt act gca act acc ggc aag      96
Leu Phe Val Asn Ile Asn Ile Val Val Gly Thr Ala Thr Thr Gly Lys
             20                  25                  30 cat tgt agc acc ggt cct atc gag tgc tgc aag cag gtc atg gat tct     144
His Cys Ser Thr Gly Pro Ile Glu Cys Cys Lys Gln Val Met Asp Ser
         35                  40                  45
```

```
aag agc cct cag gct acg gag ctt ctt acg aag aat ggc ctt ggc ctg      192
Lys Ser Pro Gln Ala Thr Glu Leu Leu Thr Lys Asn Gly Leu Gly Leu
     50                  55                  60 ggt gtc ctt gct ggc gtg aag ggt ctt gtt ggc gcg aat tgc agc cct      240
Gly Val Leu Ala Gly Val Lys Gly Leu Val Gly Ala Asn Cys Ser Pro
 65                  70                  75                  80 atc acg gca att ggt att ggc tcc ggc agc caa tgc tct ggc cag acc      288
Ile Thr Ala Ile Gly Ile Gly Ser Gly Ser Gln Cys Ser Gly Gln Thr
                     85                  90                  95 gtt tgc tgc cag aat aat aat ttc aac ggt gtt gtc gct att ggt tgc      336
Val Cys Cys Gln Asn Asn Asn Phe Asn Gly Val Val Ala Ile Gly Cys
                100                 105                 110 act ccc att aat gcc aat gtg                                          357
Thr Pro Ile Asn Ala Asn Val
            115

<210> SEQ ID NO 8
<211> LENGTH: 119
<212> TYPE: PRT
<213> ORGANISM: Unknown
<220> FEATURE:
<223> OTHER INFORMATION: basf-HypB

<400> SEQUENCE: 8

Met Val Ser Thr Phe Ile Thr Val Ala Lys Thr Leu Leu Val Ala Leu
 1               5                  10                  15

Leu Phe Val Asn Ile Asn Ile Val Val Gly Thr Ala Thr Thr Gly Lys
                20                  25                  30

His Cys Ser Thr Gly Pro Ile Glu Cys Cys Lys Gln Val Met Asp Ser
             35                  40                  45

Lys Ser Pro Gln Ala Thr Glu Leu Leu Thr Lys Asn Gly Leu Gly Leu
     50                  55                  60

Gly Val Leu Ala Gly Val Lys Gly Leu Val Gly Ala Asn Cys Ser Pro
 65                  70                  75                  80

Ile Thr Ala Ile Gly Ile Gly Ser Gly Ser Gln Cys Ser Gly Gln Thr
                 85                  90                  95

Val Cys Cys Gln Asn Asn Asn Phe Asn Gly Val Val Ala Ile Gly Cys
                100                 105                 110

Thr Pro Ile Asn Ala Asn Val
            115

<210> SEQ ID NO 9
<211> LENGTH: 408
<212> TYPE: DNA
<213> ORGANISM: Unknown
<220> FEATURE:
<221> NAME/KEY: CDS
<222> LOCATION: (1)..(408)
<223> OTHER INFORMATION: basf-sc3

<400> SEQUENCE: 9 atg ttc gcc cgt ctc ccc gtc gtg ttc ctc tac gcc ttc gtc gcg ttc       48
Met Phe Ala Arg Leu Pro Val Val Phe Leu Tyr Ala Phe Val Ala Phe
 1               5                  10                  15 ggc gcc ctc gtc gct gcc ctc cca ggt ggc cac ccg ggc acg acc acg       96
Gly Ala Leu Val Ala Ala Leu Pro Gly Gly His Pro Gly Thr Thr Thr
                20                  25                  30 ccg ccg gtt acg acg acg gtg acg gtg acc acg ccg ccc tcg acg acg      144
Pro Pro Val Thr Thr Thr Val Thr Val Thr Thr Pro Pro Ser Thr Thr
             35                  40                  45
```

```
acc atc gcc gcc ggt ggc acg tgt act acg ggg tcg ctc tct tgc tgc        192
Thr Ile Ala Ala Gly Gly Thr Cys Thr Thr Gly Ser Leu Ser Cys Cys
    50                  55                  60 aac cag gtt caa tcg gcg agc agc agc cct gtt acc gcc ctc ctc ggc        240
Asn Gln Val Gln Ser Ala Ser Ser Ser Pro Val Thr Ala Leu Leu Gly
65                  70                  75                  80 ctg ctc ggc att gtc ctc agc gac ctc aac gtt ctc gtt ggc atc agc        288
Leu Leu Gly Ile Val Leu Ser Asp Leu Asn Val Leu Val Gly Ile Ser
                85                  90                  95 tgc tct ccc ctc act gtc atc ggt gtc gga ggc agc ggc tgt tcg gcg        336
Cys Ser Pro Leu Thr Val Ile Gly Val Gly Gly Ser Gly Cys Ser Ala
            100                 105                 110 cag acc gtc tgc tgc gaa aac acc caa ttc aac ggg ctg atc aac atc        384
Gln Thr Val Cys Cys Glu Asn Thr Gln Phe Asn Gly Leu Ile Asn Ile
        115                 120                 125 ggt tgc acc ccc atc aac atc ctc                                        408
Gly Cys Thr Pro Ile Asn Ile Leu
    130                 135

<210> SEQ ID NO 10
<211> LENGTH: 136
<212> TYPE: PRT
<213> ORGANISM: Unknown
<220> FEATURE:
<223> OTHER INFORMATION: basf-sc3

<400> SEQUENCE: 10

Met Phe Ala Arg Leu Pro Val Val Phe Leu Tyr Ala Phe Val Ala Phe
1               5                   10                  15

Gly Ala Leu Val Ala Ala Leu Pro Gly Gly His Pro Gly Thr Thr Thr
                20                  25                  30

Pro Pro Val Thr Thr Thr Val Thr Val Thr Thr Pro Pro Ser Thr Thr
            35                  40                  45

Thr Ile Ala Ala Gly Gly Thr Cys Thr Thr Gly Ser Leu Ser Cys Cys
    50                  55                  60

Asn Gln Val Gln Ser Ala Ser Ser Ser Pro Val Thr Ala Leu Leu Gly
65                  70                  75                  80

Leu Leu Gly Ile Val Leu Ser Asp Leu Asn Val Leu Val Gly Ile Ser
                85                  90                  95

Cys Ser Pro Leu Thr Val Ile Gly Val Gly Gly Ser Gly Cys Ser Ala
            100                 105                 110

Gln Thr Val Cys Cys Glu Asn Thr Gln Phe Asn Gly Leu Ile Asn Ile
        115                 120                 125

Gly Cys Thr Pro Ile Asn Ile Leu
    130                 135

<210> SEQ ID NO 11
<211> LENGTH: 483
<212> TYPE: DNA
<213> ORGANISM: Unknown
<220> FEATURE:
<221> NAME/KEY: CDS
<222> LOCATION: (1)..(483)
<223> OTHER INFORMATION: basf-BASF1

<400> SEQUENCE: 11 atg aag ttc tcc gtc tcc gcc gcc gtc ctc gcc ttc gcc gcc tcc gtc         48
Met Lys Phe Ser Val Ser Ala Ala Val Leu Ala Phe Ala Ala Ser Val
1               5                   10                  15 gcc gcc ctc cct cag cac gac tcc gcc gcc ggc aac ggc aac ggc gtc         96
Ala Ala Leu Pro Gln His Asp Ser Ala Ala Gly Asn Gly Asn Gly Val
```

```
                  20                  25                  30
ggc aac aag ttc cct gtc cct gac gac gtc acc gtc aag cag gcc acc    144
Gly Asn Lys Phe Pro Val Pro Asp Asp Val Thr Val Lys Gln Ala Thr
         35                  40                  45 gac aag tgc ggc gac cag gcc cag ctc tcc tgc tgc aac aag gcc acc    192
Asp Lys Cys Gly Asp Gln Ala Gln Leu Ser Cys Cys Asn Lys Ala Thr
 50                  55                  60 tac gcc ggc gac gtc ctc acc gac atc gac gag ggc atc ctc gcc ggc    240
Tyr Ala Gly Asp Val Leu Thr Asp Ile Asp Glu Gly Ile Leu Ala Gly
 65                  70                  75                  80 ctc ctc aag aac ctc atc ggc ggc ggc tcc ggc tcc gag ggc ctc ggc    288
Leu Leu Lys Asn Leu Ile Gly Gly Gly Ser Gly Ser Glu Gly Leu Gly
             85                  90                  95 ctc ttc gac cag tgc gtc aag ctc gac ctc cag atc tcc gtc atc ggc    336
Leu Phe Asp Gln Cys Val Lys Leu Asp Leu Gln Ile Ser Val Ile Gly
                100                 105                 110 atc cct atc cag gac ctc ctc aac cag gtc aac aag cag tgc aag cag    384
Ile Pro Ile Gln Asp Leu Leu Asn Gln Val Asn Lys Gln Cys Lys Gln
        115                 120                 125 aac atc gcc tgc tgc cag aac tcc cct tcc gac gcc acc ggc tcc ctc    432
Asn Ile Ala Cys Cys Gln Asn Ser Pro Ser Asp Ala Thr Gly Ser Leu
130                 135                 140 gtc aac ctc ggc ctc ggc aac cct tgc atc cct gtc tcc ctc ctc cat    480
Val Asn Leu Gly Leu Gly Asn Pro Cys Ile Pro Val Ser Leu Leu His
145                 150                 155                 160 atg                                                                 483
Met

<210> SEQ ID NO 12
<211> LENGTH: 161
<212> TYPE: PRT
<213> ORGANISM: Unknown
<220> FEATURE:
<223> OTHER INFORMATION: basf-BASF1

<400> SEQUENCE: 12

Met Lys Phe Ser Val Ser Ala Ala Val Leu Ala Phe Ala Ala Ser Val
1               5                   10                  15

Ala Ala Leu Pro Gln His Asp Ser Ala Gly Asn Gly Asn Gly Val
            20                  25                  30

Gly Asn Lys Phe Pro Val Pro Asp Asp Val Thr Val Lys Gln Ala Thr
         35                  40                  45

Asp Lys Cys Gly Asp Gln Ala Gln Leu Ser Cys Cys Asn Lys Ala Thr
 50                  55                  60

Tyr Ala Gly Asp Val Leu Thr Asp Ile Asp Glu Gly Ile Leu Ala Gly
 65                  70                  75                  80

Leu Leu Lys Asn Leu Ile Gly Gly Gly Ser Gly Ser Glu Gly Leu Gly
             85                  90                  95

Leu Phe Asp Gln Cys Val Lys Leu Asp Leu Gln Ile Ser Val Ile Gly
                100                 105                 110

Ile Pro Ile Gln Asp Leu Leu Asn Gln Val Asn Lys Gln Cys Lys Gln
        115                 120                 125

Asn Ile Ala Cys Cys Gln Asn Ser Pro Ser Asp Ala Thr Gly Ser Leu
130                 135                 140

Val Asn Leu Gly Leu Gly Asn Pro Cys Ile Pro Val Ser Leu Leu His
145                 150                 155                 160

Met
```

<210> SEQ ID NO 13
<211> LENGTH: 465
<212> TYPE: DNA
<213> ORGANISM: Unknown
<220> FEATURE:
<221> NAME/KEY: CDS
<222> LOCATION: (1)..(465)
<223> OTHER INFORMATION: basf-BASF2

<400> SEQUENCE: 13

```
atg aag ttc tcc gtc tcc gcc gcc gtc ctc gcc ttc gcc gcc tcc gtc      48
Met Lys Phe Ser Val Ser Ala Ala Val Leu Ala Phe Ala Ala Ser Val
1               5                   10                  15 gcc gcc ctc cct cag cac gac tcc gcc gcc ggc aac ggc aac ggc gtc      96
Ala Ala Leu Pro Gln His Asp Ser Ala Ala Gly Asn Gly Asn Gly Val
                20                  25                  30 ggc aac aag ttc cct gtc cct gac gac gtc acc gtc aag cag gcc acc     144
Gly Asn Lys Phe Pro Val Pro Asp Asp Val Thr Val Lys Gln Ala Thr
            35                  40                  45 gac aag tgc ggc gac cag gcc cag ctc tcc tgc tgc aac aag gcc acc     192
Asp Lys Cys Gly Asp Gln Ala Gln Leu Ser Cys Cys Asn Lys Ala Thr
        50                  55                  60 tac gcc ggc gac gtc acc gac atc gac gag ggc atc ctc gcc ggc ctc     240
Tyr Ala Gly Asp Val Thr Asp Ile Asp Glu Gly Ile Leu Ala Gly Leu
65                  70                  75                  80 ctc aag aac ctc atc ggc ggc ggc tcc ggc tcc gag ggc ctc ggc ctc     288
Leu Lys Asn Leu Ile Gly Gly Gly Ser Gly Ser Glu Gly Leu Gly Leu
                85                  90                  95 ttc gac cag tgc gtc aag ctc gac ctc cag atc tcc gtc atc ggc atc     336
Phe Asp Gln Cys Val Lys Leu Asp Leu Gln Ile Ser Val Ile Gly Ile
                100                 105                 110 cct atc cag gac ctc ctc aac cag cag tgc aag cag aac atc gcc tgc     384
Pro Ile Gln Asp Leu Leu Asn Gln Gln Cys Lys Gln Asn Ile Ala Cys
            115                 120                 125 tgc cag aac tcc cct tcc gac gcc acc ggc tcc ctc gtc aac ctc ggc     432
Cys Gln Asn Ser Pro Ser Asp Ala Thr Gly Ser Leu Val Asn Leu Gly
        130                 135                 140 aac cct tgc atc cct gtc tcc ctc ctc cat atg                         465
Asn Pro Cys Ile Pro Val Ser Leu Leu His Met
145                 150                 155
```

<210> SEQ ID NO 14
<211> LENGTH: 155
<212> TYPE: PRT
<213> ORGANISM: Unknown
<220> FEATURE:
<223> OTHER INFORMATION: basf-BASF2

<400> SEQUENCE: 14

```
Met Lys Phe Ser Val Ser Ala Ala Val Leu Ala Phe Ala Ala Ser Val
1               5                   10                  15

Ala Ala Leu Pro Gln His Asp Ser Ala Ala Gly Asn Gly Asn Gly Val
                20                  25                  30

Gly Asn Lys Phe Pro Val Pro Asp Asp Val Thr Val Lys Gln Ala Thr
            35                  40                  45

Asp Lys Cys Gly Asp Gln Ala Gln Leu Ser Cys Cys Asn Lys Ala Thr
        50                  55                  60

Tyr Ala Gly Asp Val Thr Asp Ile Asp Glu Gly Ile Leu Ala Gly Leu
65                  70                  75                  80

Leu Lys Asn Leu Ile Gly Gly Gly Ser Gly Ser Glu Gly Leu Gly Leu
                85                  90                  95
```

```
Phe Asp Gln Cys Val Lys Leu Asp Leu Gln Ile Ser Val Ile Gly Ile
                100                 105                 110

Pro Ile Gln Asp Leu Leu Asn Gln Gln Cys Lys Gln Asn Ile Ala Cys
            115                 120                 125

Cys Gln Asn Ser Pro Ser Asp Ala Thr Gly Ser Leu Val Asn Leu Gly
        130                 135                 140

Asn Pro Cys Ile Pro Val Ser Leu Leu His Met
145                 150                 155
```

<210> SEQ ID NO 15
<211> LENGTH: 882
<212> TYPE: DNA
<213> ORGANISM: Unknown
<220> FEATURE:
<221> NAME/KEY: CDS
<222> LOCATION: (1)..(882)
<223> OTHER INFORMATION: basf-yaad

<400> SEQUENCE: 15

```
atg gct caa aca ggt act gaa cgt gta aaa cgc gga atg gca gaa atg      48
Met Ala Gln Thr Gly Thr Glu Arg Val Lys Arg Gly Met Ala Glu Met
1               5                   10                  15 caa aaa ggc ggc gtc atc atg gac gtc atc aat gcg gaa caa gcg aaa      96
Gln Lys Gly Gly Val Ile Met Asp Val Ile Asn Ala Glu Gln Ala Lys
            20                  25                  30 atc gct gaa gaa gct gga gct gtc gct gta atg gcg cta gaa cgt gtg     144
Ile Ala Glu Glu Ala Gly Ala Val Ala Val Met Ala Leu Glu Arg Val
        35                  40                  45 cca gca gat att cgc gcg gct gga gga gtt gcc cgt atg gct gac cct     192
Pro Ala Asp Ile Arg Ala Ala Gly Gly Val Ala Arg Met Ala Asp Pro
    50                  55                  60 aca atc gtg gaa gaa gta atg aat gca gta tct atc ccg gta atg gca     240
Thr Ile Val Glu Glu Val Met Asn Ala Val Ser Ile Pro Val Met Ala
65                  70                  75                  80 aaa gcg cgt atc gga cat att gtt gaa gcg cgt gtg ctt gaa gct atg     288
Lys Ala Arg Ile Gly His Ile Val Glu Ala Arg Val Leu Glu Ala Met
                85                  90                  95 ggt gtt gac tat att gat gaa agt gaa gtt ctg acg ccg gct gac gaa     336
Gly Val Asp Tyr Ile Asp Glu Ser Glu Val Leu Thr Pro Ala Asp Glu
            100                 105                 110 gaa ttt cat tta aat aaa aat gaa tac aca gtt cct ttt gtc tgt ggc     384
Glu Phe His Leu Asn Lys Asn Glu Tyr Thr Val Pro Phe Val Cys Gly
        115                 120                 125 tgc cgt gat ctt ggt gaa gca aca cgc cgt att gcg gaa ggt gct tct     432
Cys Arg Asp Leu Gly Glu Ala Thr Arg Arg Ile Ala Glu Gly Ala Ser
    130                 135                 140 atg ctt cgc aca aaa ggt gag cct gga aca ggt aat att gtt gag gct     480
Met Leu Arg Thr Lys Gly Glu Pro Gly Thr Gly Asn Ile Val Glu Ala
145                 150                 155                 160 gtt cgc cat atg cgt aaa gtt aac gct caa gtg cgc aaa gta gtt gcg     528
Val Arg His Met Arg Lys Val Asn Ala Gln Val Arg Lys Val Val Ala
                165                 170                 175 atg agt gag gat gag cta atg aca gaa gcg aaa aac cta ggt gct cct     576
Met Ser Glu Asp Glu Leu Met Thr Glu Ala Lys Asn Leu Gly Ala Pro
            180                 185                 190 tac gag ctt ctt ctt caa att aaa aaa gac ggc aag ctt cct gtc gtt     624
Tyr Glu Leu Leu Leu Gln Ile Lys Lys Asp Gly Lys Leu Pro Val Val
        195                 200                 205 aac ttt gcc gct ggc ggc gta gca act cca gct gat gct gct ctc atg     672
Asn Phe Ala Ala Gly Gly Val Ala Thr Pro Ala Asp Ala Ala Leu Met
```

```
                  210                 215                 220
atg cag ctt ggt gct gac gga gta ttt gtt ggt tct ggt att ttt aaa        720
Met Gln Leu Gly Ala Asp Gly Val Phe Val Gly Ser Gly Ile Phe Lys
225                 230                 235                 240 tca gac aac cct gct aaa ttt gcg aaa gca att gtg gaa gca aca act        768
Ser Asp Asn Pro Ala Lys Phe Ala Lys Ala Ile Val Glu Ala Thr Thr
                245                 250                 255 cac ttt act gat tac aaa tta atc gct gag ttg tca aaa gag ctt ggt        816
His Phe Thr Asp Tyr Lys Leu Ile Ala Glu Leu Ser Lys Glu Leu Gly
                260                 265                 270 act gca atg aaa ggg att gaa atc tca aac tta ctt cca gaa cag cgt        864
Thr Ala Met Lys Gly Ile Glu Ile Ser Asn Leu Leu Pro Glu Gln Arg
            275                 280                 285 atg caa gaa cgc ggc tgg                                                882
Met Gln Glu Arg Gly Trp
            290

<210> SEQ ID NO 16
<211> LENGTH: 294
<212> TYPE: PRT
<213> ORGANISM: Unknown
<220> FEATURE:
<223> OTHER INFORMATION: basf-yaad

<400> SEQUENCE: 16

Met Ala Gln Thr Gly Thr Glu Arg Val Lys Arg Gly Met Ala Glu Met
1               5                   10                  15

Gln Lys Gly Gly Val Ile Met Asp Val Ile Asn Ala Glu Gln Ala Lys
            20                  25                  30

Ile Ala Glu Glu Ala Gly Ala Val Ala Val Met Ala Leu Glu Arg Val
        35                  40                  45

Pro Ala Asp Ile Arg Ala Ala Gly Gly Val Ala Arg Met Ala Asp Pro
    50                  55                  60

Thr Ile Val Glu Glu Val Met Asn Ala Val Ser Ile Pro Val Met Ala
65                  70                  75                  80

Lys Ala Arg Ile Gly His Ile Val Glu Ala Arg Val Leu Glu Ala Met
                85                  90                  95

Gly Val Asp Tyr Ile Asp Glu Ser Glu Val Leu Thr Pro Ala Asp Glu
            100                 105                 110

Glu Phe His Leu Asn Lys Asn Glu Tyr Thr Val Pro Phe Val Cys Gly
        115                 120                 125

Cys Arg Asp Leu Gly Glu Ala Thr Arg Arg Ile Ala Glu Gly Ala Ser
    130                 135                 140

Met Leu Arg Thr Lys Gly Glu Pro Gly Thr Gly Asn Ile Val Glu Ala
145                 150                 155                 160

Val Arg His Met Arg Lys Val Asn Ala Gln Val Arg Lys Val Val Ala
                165                 170                 175

Met Ser Glu Asp Glu Leu Met Thr Glu Ala Lys Asn Leu Gly Ala Pro
            180                 185                 190

Tyr Glu Leu Leu Leu Gln Ile Lys Lys Asp Gly Lys Leu Pro Val Val
        195                 200                 205

Asn Phe Ala Ala Gly Gly Val Ala Thr Pro Ala Asp Ala Ala Leu Met
    210                 215                 220

Met Gln Leu Gly Ala Asp Gly Val Phe Val Gly Ser Gly Ile Phe Lys
225                 230                 235                 240

Ser Asp Asn Pro Ala Lys Phe Ala Lys Ala Ile Val Glu Ala Thr Thr
                245                 250                 255
```

```
His Phe Thr Asp Tyr Lys Leu Ile Ala Glu Leu Ser Lys Glu Leu Gly
            260                 265                 270

Thr Ala Met Lys Gly Ile Glu Ile Ser Asn Leu Leu Pro Glu Gln Arg
        275                 280                 285

Met Gln Glu Arg Gly Trp
    290

<210> SEQ ID NO 17
<211> LENGTH: 591
<212> TYPE: DNA
<213> ORGANISM: Unknown
<220> FEATURE:
<221> NAME/KEY: CDS
<222> LOCATION: (1)..(591)
<223> OTHER INFORMATION: basf-yaae

<400> SEQUENCE: 17 atg gga tta aca ata ggt gta cta gga ctt caa gga gca gtt aga gag      48
Met Gly Leu Thr Ile Gly Val Leu Gly Leu Gln Gly Ala Val Arg Glu
1               5                   10                  15 cac atc cat gcg att gaa gca tgc ggc gcg gct ggt ctt gtc gta aaa      96
His Ile His Ala Ile Glu Ala Cys Gly Ala Ala Gly Leu Val Val Lys
                20                  25                  30 cgt ccg gag cag ctg aac gaa gtt gac ggg ttg att ttg ccg ggc ggt     144
Arg Pro Glu Gln Leu Asn Glu Val Asp Gly Leu Ile Leu Pro Gly Gly
            35                  40                  45 gag agc acg acg atg cgc cgt ttg atc gat acg tat caa ttc atg gag     192
Glu Ser Thr Thr Met Arg Arg Leu Ile Asp Thr Tyr Gln Phe Met Glu
        50                  55                  60 ccg ctt cgt gaa ttc gct gct cag ggc aaa ccg atg ttt gga aca tgt     240
Pro Leu Arg Glu Phe Ala Ala Gln Gly Lys Pro Met Phe Gly Thr Cys
65                  70                  75                  80 gcc gga tta att ata tta gca aaa gaa att gcc ggt tca gat aat cct     288
Ala Gly Leu Ile Ile Leu Ala Lys Glu Ile Ala Gly Ser Asp Asn Pro
                85                  90                  95 cat tta ggt ctt ctg aat gtg gtt gta gaa cgt aat tca ttt ggc cgg     336
His Leu Gly Leu Leu Asn Val Val Val Glu Arg Asn Ser Phe Gly Arg
                100                 105                 110 cag gtt gac agc ttt gaa gct gat tta aca att aaa ggc ttg gac gag     384
Gln Val Asp Ser Phe Glu Ala Asp Leu Thr Ile Lys Gly Leu Asp Glu
            115                 120                 125 cct ttt act ggg gta ttc atc cgt gct ccg cat att tta gaa gct ggt     432
Pro Phe Thr Gly Val Phe Ile Arg Ala Pro His Ile Leu Glu Ala Gly
        130                 135                 140 gaa aat gtt gaa gtt cta tcg gag cat aat ggt cgt att gta gcc gcg     480
Glu Asn Val Glu Val Leu Ser Glu His Asn Gly Arg Ile Val Ala Ala
145                 150                 155                 160 aaa cag ggg caa ttc ctt ggc tgc tca ttc cat ccg gag ctg aca gaa     528
Lys Gln Gly Gln Phe Leu Gly Cys Ser Phe His Pro Glu Leu Thr Glu
                165                 170                 175 gat cac cga gtg acg cag ctg ttt gtt gaa atg gtt gag gaa tat aag     576
Asp His Arg Val Thr Gln Leu Phe Val Glu Met Val Glu Glu Tyr Lys
                180                 185                 190 caa aag gca ctt gta                                                  591
Gln Lys Ala Leu Val
        195

<210> SEQ ID NO 18
<211> LENGTH: 197
<212> TYPE: PRT
<213> ORGANISM: Unknown
```

<220> FEATURE:
<223> OTHER INFORMATION: basf-yaae

<400> SEQUENCE: 18

```
Met Gly Leu Thr Ile Gly Val Leu Gly Leu Gln Gly Ala Val Arg Glu
1               5                   10                  15

His Ile His Ala Ile Glu Ala Cys Gly Ala Ala Gly Leu Val Val Lys
            20                  25                  30

Arg Pro Glu Gln Leu Asn Glu Val Asp Gly Leu Ile Leu Pro Gly Gly
        35                  40                  45

Glu Ser Thr Thr Met Arg Arg Leu Ile Asp Thr Tyr Gln Phe Met Glu
50                  55                  60

Pro Leu Arg Glu Phe Ala Ala Gln Gly Lys Pro Met Phe Gly Thr Cys
65                  70                  75                  80

Ala Gly Leu Ile Ile Leu Ala Lys Glu Ile Ala Gly Ser Asp Asn Pro
                85                  90                  95

His Leu Gly Leu Leu Asn Val Val Val Glu Arg Asn Ser Phe Gly Arg
            100                 105                 110

Gln Val Asp Ser Phe Glu Ala Asp Leu Thr Ile Lys Gly Leu Asp Glu
        115                 120                 125

Pro Phe Thr Gly Val Phe Ile Arg Ala Pro His Ile Leu Glu Ala Gly
130                 135                 140

Glu Asn Val Glu Val Leu Ser Glu His Asn Gly Arg Ile Val Ala Ala
145                 150                 155                 160

Lys Gln Gly Gln Phe Leu Gly Cys Ser Phe His Pro Glu Leu Thr Glu
                165                 170                 175

Asp His Arg Val Thr Gln Leu Phe Val Glu Met Val Glu Glu Tyr Lys
            180                 185                 190

Gln Lys Ala Leu Val
        195
```

<210> SEQ ID NO 19
<211> LENGTH: 1329
<212> TYPE: DNA
<213> ORGANISM: Unknown
<220> FEATURE:
<221> NAME/KEY: CDS
<222> LOCATION: (1)..(1329)
<223> OTHER INFORMATION: basf-yaad-Xa-dewA-his

<400> SEQUENCE: 19

```
atg gct caa aca ggt act gaa cgt gta aaa cgc gga atg gca gaa atg      48
Met Ala Gln Thr Gly Thr Glu Arg Val Lys Arg Gly Met Ala Glu Met
1               5                   10                  15 caa aaa ggc ggc gtc atc atg gac gtc atc aat gcg gaa caa gcg aaa      96
Gln Lys Gly Gly Val Ile Met Asp Val Ile Asn Ala Glu Gln Ala Lys
            20                  25                  30 atc gct gaa gaa gct gga gct gtc gct gta atg gcg cta gaa cgt gtg     144
Ile Ala Glu Glu Ala Gly Ala Val Ala Val Met Ala Leu Glu Arg Val
        35                  40                  45 cca gca gat att cgc gcg gct gga gga gtt gcc cgt atg gct gac cct     192
Pro Ala Asp Ile Arg Ala Ala Gly Gly Val Ala Arg Met Ala Asp Pro
50                  55                  60 aca atc gtg gaa gaa gta atg aat gca gta tct atc ccg gta atg gca     240
Thr Ile Val Glu Glu Val Met Asn Ala Val Ser Ile Pro Val Met Ala
65                  70                  75                  80 aaa gcg cgt atc gga cat att gtt gaa gcg cgt gtg ctt gaa gct atg     288
Lys Ala Arg Ile Gly His Ile Val Glu Ala Arg Val Leu Glu Ala Met
                85                  90                  95
```

| | | | | | | | | | | | | | | | | |
|---|---|---|---|---|---|---|---|---|---|---|---|---|---|---|---|---|
| ggt | gtt | gac | tat | att | gat | gaa | agt | gaa | gtt | ctg | acg | ccg | gct | gac | gaa | 336 |
| Gly | Val | Asp | Tyr | Ile | Asp | Glu | Ser | Glu | Val | Leu | Thr | Pro | Ala | Asp | Glu | |
| | | | 100 | | | | 105 | | | | 110 | | | | | |
| gaa | ttt | cat | tta | aat | aaa | aat | gaa | tac | aca | gtt | cct | ttt | gtc | tgt | ggc | 384 |
| Glu | Phe | His | Leu | Asn | Lys | Asn | Glu | Tyr | Thr | Val | Pro | Phe | Val | Cys | Gly | |
| | | | 115 | | | | 120 | | | | 125 | | | | | |
| tgc | cgt | gat | ctt | ggt | gaa | gca | aca | cgc | cgt | att | gcg | gaa | ggt | gct | tct | 432 |
| Cys | Arg | Asp | Leu | Gly | Glu | Ala | Thr | Arg | Arg | Ile | Ala | Glu | Gly | Ala | Ser | |
| | 130 | | | | 135 | | | | 140 | | | | | | | |
| atg | ctt | cgc | aca | aaa | ggt | gag | cct | gga | aca | ggt | aat | att | gtt | gag | gct | 480 |
| Met | Leu | Arg | Thr | Lys | Gly | Glu | Pro | Gly | Thr | Gly | Asn | Ile | Val | Glu | Ala | |
| 145 | | | | | 150 | | | | | 155 | | | | | 160 | |
| gtt | cgc | cat | atg | cgt | aaa | gtt | aac | gct | caa | gtg | cgc | aaa | gta | gtt | gcg | 528 |
| Val | Arg | His | Met | Arg | Lys | Val | Asn | Ala | Gln | Val | Arg | Lys | Val | Val | Ala | |
| | | | | 165 | | | | | 170 | | | | | 175 | | |
| atg | agt | gag | gat | gag | cta | atg | aca | gaa | gcg | aaa | aac | cta | ggt | gct | cct | 576 |
| Met | Ser | Glu | Asp | Glu | Leu | Met | Thr | Glu | Ala | Lys | Asn | Leu | Gly | Ala | Pro | |
| | | | 180 | | | | | 185 | | | | | 190 | | | |
| tac | gag | ctt | ctt | ctt | caa | att | aaa | aaa | gac | ggc | aag | ctt | cct | gtc | gtt | 624 |
| Tyr | Glu | Leu | Leu | Leu | Gln | Ile | Lys | Lys | Asp | Gly | Lys | Leu | Pro | Val | Val | |
| | | 195 | | | | | 200 | | | | | 205 | | | | |
| aac | ttt | gcc | gct | ggc | ggc | gta | gca | act | cca | gct | gat | gct | gct | ctc | atg | 672 |
| Asn | Phe | Ala | Ala | Gly | Gly | Val | Ala | Thr | Pro | Ala | Asp | Ala | Ala | Leu | Met | |
| | 210 | | | | | 215 | | | | | 220 | | | | | |
| atg | cag | ctt | ggt | gct | gac | gga | gta | ttt | gtt | ggt | tct | ggt | att | ttt | aaa | 720 |
| Met | Gln | Leu | Gly | Ala | Asp | Gly | Val | Phe | Val | Gly | Ser | Gly | Ile | Phe | Lys | |
| 225 | | | | | 230 | | | | | 235 | | | | | 240 | |
| tca | gac | aac | cct | gct | aaa | ttt | gcg | aaa | gca | att | gtg | gaa | gca | aca | act | 768 |
| Ser | Asp | Asn | Pro | Ala | Lys | Phe | Ala | Lys | Ala | Ile | Val | Glu | Ala | Thr | Thr | |
| | | | | 245 | | | | | 250 | | | | | 255 | | |
| cac | ttt | act | gat | tac | aaa | tta | atc | gct | gag | ttg | tca | aaa | gag | ctt | ggt | 816 |
| His | Phe | Thr | Asp | Tyr | Lys | Leu | Ile | Ala | Glu | Leu | Ser | Lys | Glu | Leu | Gly | |
| | | | 260 | | | | | 265 | | | | | 270 | | | |
| act | gca | atg | aaa | ggg | att | gaa | atc | tca | aac | tta | ctt | cca | gaa | cag | cgt | 864 |
| Thr | Ala | Met | Lys | Gly | Ile | Glu | Ile | Ser | Asn | Leu | Leu | Pro | Glu | Gln | Arg | |
| | | 275 | | | | | 280 | | | | | 285 | | | | |
| atg | caa | gaa | cgc | ggc | tgg | aga | tcc | att | gaa | ggc | cgc | atg | cgc | ttc | atc | 912 |
| Met | Gln | Glu | Arg | Gly | Trp | Arg | Ser | Ile | Glu | Gly | Arg | Met | Arg | Phe | Ile | |
| | 290 | | | | | 295 | | | | | 300 | | | | | |
| gtc | tct | ctc | ctc | gcc | ttc | act | gcc | gcg | gcc | acc | gcg | acc | gcc | ctc | ccg | 960 |
| Val | Ser | Leu | Leu | Ala | Phe | Thr | Ala | Ala | Ala | Thr | Ala | Thr | Ala | Leu | Pro | |
| 305 | | | | | 310 | | | | | 315 | | | | | 320 | |
| gcc | tct | gcc | gca | aag | aac | gcg | aag | ctg | gcc | acc | tcg | gcg | gcc | ttc | gcc | 1008 |
| Ala | Ser | Ala | Ala | Lys | Asn | Ala | Lys | Leu | Ala | Thr | Ser | Ala | Ala | Phe | Ala | |
| | | | | 325 | | | | | 330 | | | | | 335 | | |
| aag | cag | gct | gaa | ggc | acc | acc | tgc | aat | gtc | ggc | tcg | atc | gct | tgc | tgc | 1056 |
| Lys | Gln | Ala | Glu | Gly | Thr | Thr | Cys | Asn | Val | Gly | Ser | Ile | Ala | Cys | Cys | |
| | | | 340 | | | | | 345 | | | | | 350 | | | |
| aac | tcc | ccc | gct | gag | acc | aac | aac | gac | agt | ctg | ttg | agc | ggt | ctg | ctc | 1104 |
| Asn | Ser | Pro | Ala | Glu | Thr | Asn | Asn | Asp | Ser | Leu | Leu | Ser | Gly | Leu | Leu | |
| | | 355 | | | | | 360 | | | | | 365 | | | | |
| ggt | gct | ggc | ctt | ctc | aac | ggg | ctc | tcg | ggc | aac | act | ggc | agc | gcc | tgc | 1152 |
| Gly | Ala | Gly | Leu | Leu | Asn | Gly | Leu | Ser | Gly | Asn | Thr | Gly | Ser | Ala | Cys | |
| | 370 | | | | | 375 | | | | | 380 | | | | | |
| gcc | aag | gcg | agc | ttg | att | gac | cag | ctg | ggt | ctg | ctc | gct | ctc | gtc | gac | 1200 |
| Ala | Lys | Ala | Ser | Leu | Ile | Asp | Gln | Leu | Gly | Leu | Leu | Ala | Leu | Val | Asp | |
| 385 | | | | | 390 | | | | | 395 | | | | | 400 | |
| cac | act | gag | gaa | ggc | ccc | gtc | tgc | aag | aac | atc | gtc | gct | tgc | tgc | cct | 1248 |
| His | Thr | Glu | Glu | Gly | Pro | Val | Cys | Lys | Asn | Ile | Val | Ala | Cys | Cys | Pro | |

```
                        405                 410                 415
gag gga acc acc aac tgt gtt gcc gtc gac aac gct ggc gct ggt acc        1296
Glu Gly Thr Thr Asn Cys Val Ala Val Asp Asn Ala Gly Ala Gly Thr
            420                 425                 430 aag gct gag gga tct cat cac cat cac cat cac                            1329
Lys Ala Glu Gly Ser His His His His His His
        435                 440
```

<210> SEQ ID NO 20
<211> LENGTH: 443
<212> TYPE: PRT
<213> ORGANISM: Unknown
<220> FEATURE:
<223> OTHER INFORMATION: basf-yaaD-Xa-dewA-his

<400> SEQUENCE: 20

```
Met Ala Gln Thr Gly Thr Glu Arg Val Lys Arg Gly Met Ala Glu Met
  1               5                  10                  15

Gln Lys Gly Gly Val Ile Met Asp Val Ile Asn Ala Glu Gln Ala Lys
             20                  25                  30

Ile Ala Glu Glu Ala Gly Ala Val Ala Val Met Ala Leu Glu Arg Val
         35                  40                  45

Pro Ala Asp Ile Arg Ala Ala Gly Gly Val Ala Arg Met Ala Asp Pro
     50                  55                  60

Thr Ile Val Glu Glu Val Met Asn Ala Val Ser Ile Pro Val Met Ala
 65                  70                  75                  80

Lys Ala Arg Ile Gly His Ile Val Glu Ala Arg Val Leu Glu Ala Met
                 85                  90                  95

Gly Val Asp Tyr Ile Asp Glu Ser Glu Val Leu Thr Pro Ala Asp Glu
            100                 105                 110

Glu Phe His Leu Asn Lys Asn Glu Tyr Thr Val Pro Phe Val Cys Gly
        115                 120                 125

Cys Arg Asp Leu Gly Glu Ala Thr Arg Arg Ile Ala Glu Gly Ala Ser
    130                 135                 140

Met Leu Arg Thr Lys Gly Glu Pro Gly Thr Gly Asn Ile Val Glu Ala
145                 150                 155                 160

Val Arg His Met Arg Lys Val Asn Ala Gln Val Arg Lys Val Val Ala
                165                 170                 175

Met Ser Glu Asp Glu Leu Met Thr Glu Ala Lys Asn Leu Gly Ala Pro
            180                 185                 190

Tyr Glu Leu Leu Leu Gln Ile Lys Lys Asp Gly Lys Leu Pro Val Val
        195                 200                 205

Asn Phe Ala Ala Gly Gly Val Ala Thr Pro Ala Asp Ala Ala Leu Met
    210                 215                 220

Met Gln Leu Gly Ala Asp Gly Val Phe Val Gly Ser Gly Ile Phe Lys
225                 230                 235                 240

Ser Asp Asn Pro Ala Lys Phe Ala Lys Ala Ile Val Glu Ala Thr Thr
                245                 250                 255

His Phe Thr Asp Tyr Lys Leu Ile Ala Glu Leu Ser Lys Glu Leu Gly
            260                 265                 270

Thr Ala Met Lys Gly Ile Glu Ile Ser Asn Leu Leu Pro Glu Gln Arg
        275                 280                 285

Met Gln Glu Arg Gly Trp Arg Ser Ile Glu Gly Arg Met Arg Phe Ile
    290                 295                 300

Val Ser Leu Leu Ala Phe Thr Ala Ala Ala Thr Ala Thr Ala Leu Pro
305                 310                 315                 320
```

```
Ala Ser Ala Ala Lys Asn Ala Lys Leu Ala Thr Ser Ala Ala Phe Ala
            325                 330                 335

Lys Gln Ala Glu Gly Thr Thr Cys Asn Val Gly Ser Ile Ala Cys Cys
        340                 345                 350

Asn Ser Pro Ala Glu Thr Asn Asn Asp Ser Leu Leu Ser Gly Leu Leu
            355                 360                 365

Gly Ala Gly Leu Leu Asn Gly Leu Ser Gly Asn Thr Gly Ser Ala Cys
    370                 375                 380

Ala Lys Ala Ser Leu Ile Asp Gln Leu Gly Leu Leu Ala Leu Val Asp
385                 390                 395                 400

His Thr Glu Glu Gly Pro Val Cys Lys Asn Ile Val Ala Cys Cys Pro
                405                 410                 415

Glu Gly Thr Thr Asn Cys Val Ala Val Asp Asn Ala Gly Ala Gly Thr
            420                 425                 430

Lys Ala Glu Gly Ser His His His His His His
        435                 440

<210> SEQ ID NO 21
<211> LENGTH: 1395
<212> TYPE: DNA
<213> ORGANISM: Unknown
<220> FEATURE:
<221> NAME/KEY: CDS
<222> LOCATION: (1)..(1395)
<223> OTHER INFORMATION: basf-yaad-Xa-rodA-his

<400> SEQUENCE: 21 atg gct caa aca ggt act gaa cgt gta aaa cgc gga atg gca gaa atg      48
Met Ala Gln Thr Gly Thr Glu Arg Val Lys Arg Gly Met Ala Glu Met
1               5                   10                  15 caa aaa ggc ggc gtc atc atg gac gtc atc aat gcg gaa caa gcg aaa      96
Gln Lys Gly Gly Val Ile Met Asp Val Ile Asn Ala Glu Gln Ala Lys
            20                  25                  30 atc gct gaa gaa gct gga gct gtc gct gta atg gcg cta gaa cgt gtg     144
Ile Ala Glu Glu Ala Gly Ala Val Ala Val Met Ala Leu Glu Arg Val
        35                  40                  45 cca gca gat att cgc gcg gct gga gga gtt gcc cgt atg gct gac cct     192
Pro Ala Asp Ile Arg Ala Ala Gly Gly Val Ala Arg Met Ala Asp Pro
    50                  55                  60 aca atc gtg gaa gaa gta atg aat gca gta tct atc ccg gta atg gca     240
Thr Ile Val Glu Glu Val Met Asn Ala Val Ser Ile Pro Val Met Ala
65                  70                  75                  80 aaa gcg cgt atc gga cat att gtt gaa gcg cgt gtg ctt gaa gct atg     288
Lys Ala Arg Ile Gly His Ile Val Glu Ala Arg Val Leu Glu Ala Met
                85                  90                  95 ggt gtt gac tat att gat gaa agt gaa gtt ctg acg ccg gct gac gaa     336
Gly Val Asp Tyr Ile Asp Glu Ser Glu Val Leu Thr Pro Ala Asp Glu
            100                 105                 110 gaa ttt cat tta aat aaa aat gaa tac aca gtt cct ttt gtc tgt ggc     384
Glu Phe His Leu Asn Lys Asn Glu Tyr Thr Val Pro Phe Val Cys Gly
        115                 120                 125 tgc cgt gat ctt ggt gaa gca aca cgc cgt att gcg gaa ggt gct tct     432
Cys Arg Asp Leu Gly Glu Ala Thr Arg Arg Ile Ala Glu Gly Ala Ser
    130                 135                 140 atg ctt cgc aca aaa ggt gag cct gga aca ggt aat att gtt gag gct     480
Met Leu Arg Thr Lys Gly Glu Pro Gly Thr Gly Asn Ile Val Glu Ala
145                 150                 155                 160 gtt cgc cat atg cgt aaa gtt aac gct caa gtg cgc aaa gta gtt gcg     528
Val Arg His Met Arg Lys Val Asn Ala Gln Val Arg Lys Val Val Ala
```

```
                     165                 170                 175
atg agt gag gat gag cta atg aca gaa gcg aaa aac cta ggt gct cct    576
Met Ser Glu Asp Glu Leu Met Thr Glu Ala Lys Asn Leu Gly Ala Pro
            180                 185                 190 tac gag ctt ctt ctt caa att aaa aaa gac ggc aag ctt cct gtc gtt    624
Tyr Glu Leu Leu Leu Gln Ile Lys Lys Asp Gly Lys Leu Pro Val Val
        195                 200                 205 aac ttt gcc gct ggc ggc gta gca act cca gct gat gct gct ctc atg    672
Asn Phe Ala Ala Gly Gly Val Ala Thr Pro Ala Asp Ala Ala Leu Met
    210                 215                 220 atg cag ctt ggt gct gac gga gta ttt gtt ggt tct ggt att ttt aaa    720
Met Gln Leu Gly Ala Asp Gly Val Phe Val Gly Ser Gly Ile Phe Lys
225                 230                 235                 240 tca gac aac cct gct aaa ttt gcg aaa gca att gtg gaa gca aca act    768
Ser Asp Asn Pro Ala Lys Phe Ala Lys Ala Ile Val Glu Ala Thr Thr
                245                 250                 255 cac ttt act gat tac aaa tta atc gct gag ttg tca aaa gag ctt ggt    816
His Phe Thr Asp Tyr Lys Leu Ile Ala Glu Leu Ser Lys Glu Leu Gly
            260                 265                 270 act gca atg aaa ggg att gaa atc tca aac tta ctt cca gaa cag cgt    864
Thr Ala Met Lys Gly Ile Glu Ile Ser Asn Leu Leu Pro Glu Gln Arg
        275                 280                 285 atg caa gaa cgc ggc tgg aga tct att gaa ggc cgc atg aag ttc tcc    912
Met Gln Glu Arg Gly Trp Arg Ser Ile Glu Gly Arg Met Lys Phe Ser
    290                 295                 300 att gct gcc gct gtc gtt gct ttc gcc gcc tcc gtc gcg gcc ctc cct    960
Ile Ala Ala Ala Val Val Ala Phe Ala Ala Ser Val Ala Ala Leu Pro
305                 310                 315                 320 cct gcc cat gat tcc cag ttc gct ggc aat ggt gtt ggc aac aag ggc   1008
Pro Ala His Asp Ser Gln Phe Ala Gly Asn Gly Val Gly Asn Lys Gly
                325                 330                 335 aac agc aac gtc aag ttc cct gtc ccc gaa aac gtg acc gtc aag cag   1056
Asn Ser Asn Val Lys Phe Pro Val Pro Glu Asn Val Thr Val Lys Gln
            340                 345                 350 gcc tcc gac aag tgc ggt gac cag gcc cag ctc tct tgc tgc aac aag   1104
Ala Ser Asp Lys Cys Gly Asp Gln Ala Gln Leu Ser Cys Cys Asn Lys
        355                 360                 365 gcc acg tac gcc ggt gac acc aca acc gtt gat gag ggt ctt ctg tct   1152
Ala Thr Tyr Ala Gly Asp Thr Thr Thr Val Asp Glu Gly Leu Leu Ser
    370                 375                 380 ggt gcc ctc agc ggc ctc atc ggc gcc ggg tct ggt gcc gaa ggt ctt   1200
Gly Ala Leu Ser Gly Leu Ile Gly Ala Gly Ser Gly Ala Glu Gly Leu
385                 390                 395                 400 ggt ctc ttc gat cag tgc tcc aag ctt gat gtt gct gtc ctc att ggc   1248
Gly Leu Phe Asp Gln Cys Ser Lys Leu Asp Val Ala Val Leu Ile Gly
                405                 410                 415 atc caa gat ctt gtc aac cag aag tgc aag caa aac att gcc tgc tgc   1296
Ile Gln Asp Leu Val Asn Gln Lys Cys Lys Gln Asn Ile Ala Cys Cys
            420                 425                 430 cag aac tcc ccc tcc agc gcg gat ggc aac ctt att ggt gtc ggt ctc   1344
Gln Asn Ser Pro Ser Ser Ala Asp Gly Asn Leu Ile Gly Val Gly Leu
        435                 440                 445 cct tgc gtt gcc ctt ggc tcc atc ctc gga tct cat cac cat cac cat   1392
Pro Cys Val Ala Leu Gly Ser Ile Leu Gly Ser His His His His His
    450                 455                 460 cac                                                                1395
His
465
```

<210> SEQ ID NO 22
<211> LENGTH: 465
<212> TYPE: PRT
<213> ORGANISM: Unknown
<220> FEATURE:
<223> OTHER INFORMATION: basf-yaaD-Xa-rodA-his

<400> SEQUENCE: 22

```
Met Ala Gln Thr Gly Thr Glu Arg Val Lys Arg Gly Met Ala Glu Met
1               5                   10                  15

Gln Lys Gly Gly Val Ile Met Asp Val Ile Asn Ala Glu Gln Ala Lys
            20                  25                  30

Ile Ala Glu Glu Ala Gly Ala Val Ala Val Met Ala Leu Glu Arg Val
        35                  40                  45

Pro Ala Asp Ile Arg Ala Ala Gly Gly Val Ala Arg Met Ala Asp Pro
    50                  55                  60

Thr Ile Val Glu Glu Val Met Asn Ala Val Ser Ile Pro Val Met Ala
65                  70                  75                  80

Lys Ala Arg Ile Gly His Ile Val Glu Ala Arg Val Leu Glu Ala Met
                85                  90                  95

Gly Val Asp Tyr Ile Asp Glu Ser Glu Val Leu Thr Pro Ala Asp Glu
            100                 105                 110

Glu Phe His Leu Asn Lys Asn Glu Tyr Thr Val Pro Phe Val Cys Gly
        115                 120                 125

Cys Arg Asp Leu Gly Glu Ala Thr Arg Arg Ile Ala Glu Gly Ala Ser
    130                 135                 140

Met Leu Arg Thr Lys Gly Glu Pro Gly Thr Gly Asn Ile Val Glu Ala
145                 150                 155                 160

Val Arg His Met Arg Lys Val Asn Ala Gln Val Arg Lys Val Val Ala
                165                 170                 175

Met Ser Glu Asp Glu Leu Met Thr Glu Ala Lys Asn Leu Gly Ala Pro
            180                 185                 190

Tyr Glu Leu Leu Leu Gln Ile Lys Lys Asp Gly Lys Leu Pro Val Val
        195                 200                 205

Asn Phe Ala Ala Gly Gly Val Ala Thr Pro Ala Asp Ala Ala Leu Met
    210                 215                 220

Met Gln Leu Gly Ala Asp Gly Val Phe Val Gly Ser Gly Ile Phe Lys
225                 230                 235                 240

Ser Asp Asn Pro Ala Lys Phe Ala Lys Ala Ile Val Glu Ala Thr Thr
                245                 250                 255

His Phe Thr Asp Tyr Lys Leu Ile Ala Glu Leu Ser Lys Glu Leu Gly
            260                 265                 270

Thr Ala Met Lys Gly Ile Glu Ile Ser Asn Leu Leu Pro Glu Gln Arg
        275                 280                 285

Met Gln Glu Arg Gly Trp Arg Ser Ile Glu Gly Arg Met Lys Phe Ser
    290                 295                 300

Ile Ala Ala Ala Val Val Ala Phe Ala Ala Ser Val Ala Ala Leu Pro
305                 310                 315                 320

Pro Ala His Asp Ser Gln Phe Ala Gly Asn Gly Val Gly Asn Lys Gly
                325                 330                 335

Asn Ser Asn Val Lys Phe Pro Val Pro Glu Asn Val Thr Val Lys Gln
            340                 345                 350

Ala Ser Asp Lys Cys Gly Asp Gln Ala Gln Leu Ser Cys Cys Asn Lys
        355                 360                 365

Ala Thr Tyr Ala Gly Asp Thr Thr Val Asp Glu Gly Leu Leu Ser
```

```
                370                 375                 380
Gly Ala Leu Ser Gly Leu Ile Gly Ala Gly Ser Gly Ala Glu Gly Leu
385                 390                 395                 400

Gly Leu Phe Asp Gln Cys Ser Lys Leu Asp Val Ala Val Leu Ile Gly
            405                 410                 415

Ile Gln Asp Leu Val Asn Gln Lys Cys Lys Gln Asn Ile Ala Cys Cys
        420                 425                 430

Gln Asn Ser Pro Ser Ser Ala Asp Gly Asn Leu Ile Gly Val Gly Leu
    435                 440                 445

Pro Cys Val Ala Leu Gly Ser Ile Leu Gly Ser His His His His
450                 455                 460

His
465

<210> SEQ ID NO 23
<211> LENGTH: 1407
<212> TYPE: DNA
<213> ORGANISM: Unknown
<220> FEATURE:
<221> NAME/KEY: CDS
<222> LOCATION: (1)..(1407)
<223> OTHER INFORMATION: basf-yaad-Xa-BASF1-his

<400> SEQUENCE: 23 atg gct caa aca ggt act gaa cgt gta aaa cgc gga atg gca gaa atg      48
Met Ala Gln Thr Gly Thr Glu Arg Val Lys Arg Gly Met Ala Glu Met
1               5                   10                  15 caa aaa ggc ggc gtc atc atg gac gtc atc aat gcg gaa caa gcg aaa      96
Gln Lys Gly Gly Val Ile Met Asp Val Ile Asn Ala Glu Gln Ala Lys
            20                  25                  30 atc gct gaa gaa gct gga gct gtc gct gta atg gcg cta gaa cgt gtg     144
Ile Ala Glu Glu Ala Gly Ala Val Ala Val Met Ala Leu Glu Arg Val
        35                  40                  45 cca gca gat att cgc gcg gct gga gga gtt gcc cgt atg gct gac cct     192
Pro Ala Asp Ile Arg Ala Ala Gly Gly Val Ala Arg Met Ala Asp Pro
    50                  55                  60 aca atc gtg gaa gaa gta atg aat gca gta tct atc ccg gta atg gca     240
Thr Ile Val Glu Glu Val Met Asn Ala Val Ser Ile Pro Val Met Ala
65                  70                  75                  80 aaa gcg cgt atc gga cat att gtt gaa gcg cgt gtg ctt gaa gct atg     288
Lys Ala Arg Ile Gly His Ile Val Glu Ala Arg Val Leu Glu Ala Met
                85                  90                  95 ggt gtt gac tat att gat gaa agt gaa gtt ctg acg ccg gct gac gaa     336
Gly Val Asp Tyr Ile Asp Glu Ser Glu Val Leu Thr Pro Ala Asp Glu
            100                 105                 110 gaa ttt cat tta aat aaa aat gaa tac aca gtt cct ttt gtc tgt ggc     384
Glu Phe His Leu Asn Lys Asn Glu Tyr Thr Val Pro Phe Val Cys Gly
        115                 120                 125 tgc cgt gat ctt ggt gaa gca aca cgc cgt att gcg gaa ggt gct tct     432
Cys Arg Asp Leu Gly Glu Ala Thr Arg Arg Ile Ala Glu Gly Ala Ser
    130                 135                 140 atg ctt cgc aca aaa ggt gag cct gga aca ggt aat att gtt gag gct     480
Met Leu Arg Thr Lys Gly Glu Pro Gly Thr Gly Asn Ile Val Glu Ala
145                 150                 155                 160 gtt cgc cat atg cgt aaa gtt aac gct caa gtg cgc aaa gta gtt gcg     528
Val Arg His Met Arg Lys Val Asn Ala Gln Val Arg Lys Val Val Ala
                165                 170                 175 atg agt gag gat gag cta atg aca gaa gcg aaa aac cta ggt gct cct     576
Met Ser Glu Asp Glu Leu Met Thr Glu Ala Lys Asn Leu Gly Ala Pro
            180                 185                 190
```

| | | |
|---|---|---|
| tac gag ctt ctt ctt caa att aaa aaa gac ggc aag ctt cct gtc gtt<br>Tyr Glu Leu Leu Leu Gln Ile Lys Lys Asp Gly Lys Leu Pro Val Val<br>          195                  200                  205 | 624 |
| aac ttt gcc gct ggc ggc gta gca act cca gct gat gct gct ctc atg<br>Asn Phe Ala Ala Gly Gly Val Ala Thr Pro Ala Asp Ala Ala Leu Met<br>210                  215                  220 | 672 |
| atg cag ctt ggt gct gac gga gta ttt gtt ggt tct ggt att ttt aaa<br>Met Gln Leu Gly Ala Asp Gly Val Phe Val Gly Ser Gly Ile Phe Lys<br>225                  230                  235                  240 | 720 |
| tca gac aac cct gct aaa ttt gcg aaa gca att gtg gaa gca aca act<br>Ser Asp Asn Pro Ala Lys Phe Ala Lys Ala Ile Val Glu Ala Thr Thr<br>          245                  250                  255 | 768 |
| cac ttt act gat tac aaa tta atc gct gag ttg tca aaa gag ctt ggt<br>His Phe Thr Asp Tyr Lys Leu Ile Ala Glu Leu Ser Lys Glu Leu Gly<br>          260                  265                  270 | 816 |
| act gca atg aaa ggg att gaa atc tca aac tta ctt cca gaa cag cgt<br>Thr Ala Met Lys Gly Ile Glu Ile Ser Asn Leu Leu Pro Glu Gln Arg<br>          275                  280                  285 | 864 |
| atg caa gaa cgc ggc tgg aga tct att gaa ggc cgc atg aag ttc tcc<br>Met Gln Glu Arg Gly Trp Arg Ser Ile Glu Gly Arg Met Lys Phe Ser<br>290                  295                  300 | 912 |
| gtc tcc gcc gcc gtc ctc gcc ttc gcc gcc tcc gtc gcc gcc ctc cct<br>Val Ser Ala Ala Val Leu Ala Phe Ala Ala Ser Val Ala Ala Leu Pro<br>305                  310                  315                  320 | 960 |
| cag cac gac tcc gcc gcc ggc aac ggc aac ggc gtc ggc aac aag ttc<br>Gln His Asp Ser Ala Ala Gly Asn Gly Asn Gly Val Gly Asn Lys Phe<br>                  325                  330                  335 | 1008 |
| cct gtc cct gac gac gtc acc gtc aag cag gcc acc gac aag tgc ggc<br>Pro Val Pro Asp Asp Val Thr Val Lys Gln Ala Thr Asp Lys Cys Gly<br>                  340                  345                  350 | 1056 |
| gac cag gcc cag ctc tcc tgc tgc aac aag gcc acc tac gcc ggc gac<br>Asp Gln Ala Gln Leu Ser Cys Cys Asn Lys Ala Thr Tyr Ala Gly Asp<br>          355                  360                  365 | 1104 |
| gtc ctc acc gac atc gac gag ggc atc ctc gcc ggc ctc ctc aag aac<br>Val Leu Thr Asp Ile Asp Glu Gly Ile Leu Ala Gly Leu Leu Lys Asn<br>370                  375                  380 | 1152 |
| ctc atc ggc ggc ggc tcc ggc tcc gag ggc ctc ggc ctc ttc gac cag<br>Leu Ile Gly Gly Gly Ser Gly Ser Glu Gly Leu Gly Leu Phe Asp Gln<br>385                  390                  395                  400 | 1200 |
| tgc gtc aag ctc gac ctc cag atc tcc gtc atc ggc atc cct atc cag<br>Cys Val Lys Leu Asp Leu Gln Ile Ser Val Ile Gly Ile Pro Ile Gln<br>                  405                  410                  415 | 1248 |
| gac ctc ctc aac cag gtc aac aag cag tgc aag cag aac atc gcc tgc<br>Asp Leu Leu Asn Gln Val Asn Lys Gln Cys Lys Gln Asn Ile Ala Cys<br>          420                  425                  430 | 1296 |
| tgc cag aac tcc cct tcc gac gcc acc ggc tcc ctc gtc aac ctc ggc<br>Cys Gln Asn Ser Pro Ser Asp Ala Thr Gly Ser Leu Val Asn Leu Gly<br>          435                  440                  445 | 1344 |
| ctc ggc aac cct tgc atc cct gtc tcc ctc ctc cat atg gga tct cat<br>Leu Gly Asn Pro Cys Ile Pro Val Ser Leu Leu His Met Gly Ser His<br>          450                  455                  460 | 1392 |
| cac cat cac cat cac<br>His His His His His<br>465 | 1407 |

<210> SEQ ID NO 24
<211> LENGTH: 469
<212> TYPE: PRT
<213> ORGANISM: Unknown
<220> FEATURE:

<223> OTHER INFORMATION: basf-yaaD-Xa-BASF1-his

<400> SEQUENCE: 24

```
Met Ala Gln Thr Gly Thr Glu Arg Val Lys Arg Gly Met Ala Glu Met
  1               5                  10                  15

Gln Lys Gly Gly Val Ile Met Asp Val Ile Asn Ala Glu Gln Ala Lys
             20                  25                  30

Ile Ala Glu Glu Ala Gly Ala Val Ala Val Met Ala Leu Glu Arg Val
         35                  40                  45

Pro Ala Asp Ile Arg Ala Ala Gly Gly Val Ala Arg Met Ala Asp Pro
     50                  55                  60

Thr Ile Val Glu Glu Val Met Asn Ala Val Ser Ile Pro Val Met Ala
 65                  70                  75                  80

Lys Ala Arg Ile Gly His Ile Val Glu Ala Arg Val Leu Glu Ala Met
                 85                  90                  95

Gly Val Asp Tyr Ile Asp Glu Ser Glu Val Leu Thr Pro Ala Asp Glu
            100                 105                 110

Glu Phe His Leu Asn Lys Asn Glu Tyr Thr Val Pro Phe Val Cys Gly
        115                 120                 125

Cys Arg Asp Leu Gly Glu Ala Thr Arg Arg Ile Ala Glu Gly Ala Ser
    130                 135                 140

Met Leu Arg Thr Lys Gly Glu Pro Gly Thr Gly Asn Ile Val Glu Ala
145                 150                 155                 160

Val Arg His Met Arg Lys Val Asn Ala Gln Val Arg Lys Val Val Ala
                165                 170                 175

Met Ser Glu Asp Glu Leu Met Thr Glu Ala Lys Asn Leu Gly Ala Pro
            180                 185                 190

Tyr Glu Leu Leu Leu Gln Ile Lys Lys Asp Gly Lys Leu Pro Val Val
        195                 200                 205

Asn Phe Ala Ala Gly Gly Val Ala Thr Pro Ala Asp Ala Ala Leu Met
    210                 215                 220

Met Gln Leu Gly Ala Asp Gly Val Phe Val Gly Ser Gly Ile Phe Lys
225                 230                 235                 240

Ser Asp Asn Pro Ala Lys Phe Ala Lys Ala Ile Val Glu Ala Thr Thr
                245                 250                 255

His Phe Thr Asp Tyr Lys Leu Ile Ala Glu Leu Ser Lys Glu Leu Gly
            260                 265                 270

Thr Ala Met Lys Gly Ile Glu Ile Ser Asn Leu Leu Pro Glu Gln Arg
        275                 280                 285

Met Gln Glu Arg Gly Trp Arg Ser Ile Glu Gly Arg Met Lys Phe Ser
    290                 295                 300

Val Ser Ala Ala Val Leu Ala Phe Ala Ala Ser Val Ala Ala Leu Pro
305                 310                 315                 320

Gln His Asp Ser Ala Ala Gly Asn Gly Asn Gly Val Gly Asn Lys Phe
                325                 330                 335

Pro Val Pro Asp Asp Val Thr Val Lys Gln Ala Thr Asp Lys Cys Gly
            340                 345                 350

Asp Gln Ala Gln Leu Ser Cys Cys Asn Lys Ala Thr Tyr Ala Gly Asp
        355                 360                 365

Val Leu Thr Asp Ile Asp Glu Gly Ile Leu Ala Gly Leu Leu Lys Asn
    370                 375                 380

Leu Ile Gly Gly Gly Ser Gly Ser Glu Gly Leu Gly Leu Phe Asp Gln
385                 390                 395                 400
```

Cys Val Lys Leu Asp Leu Gln Ile Ser Val Ile Gly Ile Pro Ile Gln
                405                 410                 415

Asp Leu Leu Asn Gln Val Asn Lys Gln Cys Lys Gln Asn Ile Ala Cys
            420                 425                 430

Cys Gln Asn Ser Pro Ser Asp Ala Thr Gly Ser Leu Val Asn Leu Gly
        435                 440                 445

Leu Gly Asn Pro Cys Ile Pro Val Ser Leu Leu His Met Gly Ser His
    450                 455                 460

His His His His His
465

<210> SEQ ID NO 25
<211> LENGTH: 28
<212> TYPE: DNA
<213> ORGANISM: Unknown
<220> FEATURE:
<223> OTHER INFORMATION: Hal570 oligonucleotide

<400> SEQUENCE: 25
gcgcgcccat ggctcaaaca ggtactga                                      28

<210> SEQ ID NO 26
<211> LENGTH: 28
<212> TYPE: DNA
<213> ORGANISM: Unknown
<220> FEATURE:
<223> OTHER INFORMATION: Hal571 oligonucleotide

<400> SEQUENCE: 26
gcagatctcc agccgcgttc ttgcatac                                      28

<210> SEQ ID NO 27
<211> LENGTH: 30
<212> TYPE: DNA
<213> ORGANISM: Unknown
<220> FEATURE:
<223> OTHER INFORMATION: Hal572 oligonucleotide

<400> SEQUENCE: 27
ggccatggga ttaacaatag gtgtactagg                                    30

<210> SEQ ID NO 28
<211> LENGTH: 33
<212> TYPE: DNA
<213> ORGANISM: Unknown
<220> FEATURE:
<223> OTHER INFORMATION: Hal573 oligonucleotide

<400> SEQUENCE: 28
gcagatctta caagtgcctt ttgcttatat tcc                                33

<210> SEQ ID NO 29
<211> LENGTH: 38
<212> TYPE: DNA
<213> ORGANISM: Unknown
<220> FEATURE:
<223> OTHER INFORMATION: KaM416 oligonucleotide

<400> SEQUENCE: 29
gcagcccatc agggatccct cagccttggt accagcgc                           38

<210> SEQ ID NO 30
<211> LENGTH: 50
<212> TYPE: DNA

```
<213> ORGANISM: Unknown
<220> FEATURE:
<223> OTHER INFORMATION: KaM417 oligonucleotide

<400> SEQUENCE: 30
cccgtagcta gtggatccat tgaaggccgc atgaagttct ccgtctccgc                50

<210> SEQ ID NO 31
<211> LENGTH: 45
<212> TYPE: DNA
<213> ORGANISM: Unknown
<220> FEATURE:
<223> OTHER INFORMATION: KaM434 oligonucleotide

<400> SEQUENCE: 31
gctaagcgga tccattgaag gccgcatgaa gttctccatt gctgc                     45

<210> SEQ ID NO 32
<211> LENGTH: 30
<212> TYPE: DNA
<213> ORGANISM: Unknown
<220> FEATURE:
<223> OTHER INFORMATION: KaM435 oligonucleotide

<400> SEQUENCE: 32
ccaatgggga tccgaggatg gagccaaggg                                      30

<210> SEQ ID NO 33
<211> LENGTH: 38
<212> TYPE: DNA
<213> ORGANISM: Unknown
<220> FEATURE:
<223> OTHER INFORMATION: KaM418 oligonucleotide

<400> SEQUENCE: 33
ctgccattca ggggatccca tatggaggag ggagacag                             38

<210> SEQ ID NO 34
<211> LENGTH: 32
<212> TYPE: DNA
<213> ORGANISM: Unknown
<220> FEATURE:
<223> OTHER INFORMATION: KaM464 oligonucleotide

<400> SEQUENCE: 34
cgttaaggat ccgaggatgt tgatgggggt gc                                   32

<210> SEQ ID NO 35
<211> LENGTH: 35
<212> TYPE: DNA
<213> ORGANISM: Unknown
<220> FEATURE:
<223> OTHER INFORMATION: KaM465 oligonucleotide

<400> SEQUENCE: 35
gctaacagat ctatgttcgc ccgtctcccc gtcgt                                35
```